(12) United States Patent
Wu et al.

(10) Patent No.: US 9,696,304 B2
(45) Date of Patent: Jul. 4, 2017

(54) METHODS FOR DETECTING A BIOMARKER BY ALTERNATING CURRENT ELECTROKINETICS

(71) Applicant: University of Tennessee Research Foundation, Knoxville, TN (US)

(72) Inventors: Jie Wu, Knoxville, TN (US); Shigetoshi Eda, Knoxville, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 15/392,412

(22) Filed: Dec. 28, 2016

(65) Prior Publication Data

US 2017/0108493 A1    Apr. 20, 2017

Related U.S. Application Data

(63) Continuation-in-part of application No. 14/374,312, filed as application No. PCT/US2013/022447 on Jan. 22, 2013, now Pat. No. 9,568,444.

(60) Provisional application No. 61/591,713, filed on Jan. 27, 2012.

(51) Int. Cl.
*G01N 27/02* (2006.01)
*G01N 33/543* (2006.01)

(52) U.S. Cl.
CPC ....... *G01N 33/5438* (2013.01); *G01N 27/021* (2013.01)

(58) Field of Classification Search
None
See application file for complete search history.

(56) References Cited

U.S. PATENT DOCUMENTS

| 7,063,778 B2 | 6/2006 | Mpholo et al. |
|---|---|---|
| 7,422,869 B2 | 9/2008 | Eda et al. |
| 7,517,955 B2 | 4/2009 | Oliver et al. |
| 7,713,715 B2 | 5/2010 | Speer et al. |
| 7,812,147 B2 | 10/2010 | Oliver et al. |
| 2005/0112544 A1 | 5/2005 | Xu et al. |
| 2006/0237310 A1 | 10/2006 | Patel et al. |
| 2009/0117571 A1 | 5/2009 | Solanki et al. |

OTHER PUBLICATIONS

Yang, Kai, "In Situ Preconcentration by AC Electrokinetics for Rapid and Sensitive Nanoparticle Detection," PhD dissertation, University of Tennessee, Aug. 30, 2011, pp. 1-139.
Tsouti et al., "Capacitive Microsystems for Biological Sensing", Biosensors & Bioelectronics, vol. 27, Issue 1, pp. 1-11, Sep. 15, 2011.

(Continued)

*Primary Examiner* — Rebecca Martinez
(74) *Attorney, Agent, or Firm* — Andrews Kurth Kenyon LLP

(57) ABSTRACT

Methods are described for detecting pathogens, infectious diseases, and physiological conditions by quantifying change of impedance over time of when a biological sample is applied onto a lab-on-a-chip. The lab-on-a-chip utilizes alternating-current electrokinetic (ACEK) phenomena such that molecules move or are carried in an electric field generated by the application of an electrical signal of predetermined magnitude and frequency to an electrode array of the lab-on-a-chip.

17 Claims, 36 Drawing Sheets

(56) References Cited

OTHER PUBLICATIONS

Krishnan et al., "Alternating Current Electrokinetic Separation and Detection of DNA Nanoparticles in High-conductance Solutions," Electrophoresis, Special Issue: Miniaturization in Asia Pacific, vol. 29, Issue 9, pp. 1765-1774, Apr. 7, 2008.

Germishuizen et al., "Influence of Alternating Current Electrokinetic Forces and Torque on the Elongation of Immobilized DNA", Journal of Applied Physics, vol. 97, Issue 1, pp. 014702-1 to 014702-7, Jan. 31, 2005.

Li et al., "Dielectrophoretic responses of DNA and fluorophore in physiological solution of impedimetric characterization," Biosensors and Bioelectronics, vol. 41, pp. 649-655, Sep. 28, 2012.

Shafran et al., "Seroreactivities Against *Saccharomyces cerevisiae* and *Mycobacterium avium* subsp. paratuberculosis p35 and p36 Antigens in Crohn's Disease Patients," Digestive Diseases and Sciences, vol. 47, No. 9, Sep. 2002, pp. 2079-2081.

Chai et al., "Label-Free Toxin Detection by Means of Time-Resolved Electrochemical Impedance Spectroscopy", Sensors, 10, pp. 655-669, published online Jan. 18, 2010.

Laczka et al., "Detection of *Escherichia coli* and *Salmonella typhimurium* Using Interdigitated Microelectrode Capacitive Immunosensors: The Importance of Transducer Geometry", Analytical Chemistry, vol. 80, No. 19, Oct. 1, 2008, pp. 7239-7247.

Berdat et al., "Label-free detection of DNA with interdigitated micro-electrodes in a fluidic cell", Lab Chip, vol. 8, No. 2, Jan. 1, 2008, pp. 302-308.

Liu et al., "Development of an AC electrokinetics-based immunoassay system for on-site serodiagnosis of infectious diseases", Sensors and Actuators A, Elsevier Sequoia S.A., vol. 171, No. 2, Aug. 9, 2011, pp. 406-413.

Extended European Search Report, mailed Sep. 4, 2015, from corresponding EP Patent Application No. 13741296.1, filed Jan. 22, 2013.

Henning et al., "Dielectrophoresis of DNA: Quantification by impedance measurements", American Institute of Physics: Biomicrofluidics, v.4 (2) available online Jun. 29, 2010, 022803, pp. 1-9.

Australian Examination Report, issued Nov. 26, 2015, from corresponding Australian Patent Application No. 2013212574, filed Jul. 11, 2014.

Blind Test Results for Johne's Disease
(Twenty Serum Samples)

|  | Negative | Positive |
|---|---|---|
| Change Rate of C(‰/min) | -4.052 | -24.9039 |
|  | -8.4539 | -52.2964 |
|  | 8.2321 | -28.8861 |
|  | 2.7727 | -65.0035 |
|  | -7.329 | -33.2244 |
|  | -6.4258 | -48.2316 |
|  | 5.3198 | -15.0843 |
|  | 3.3915 | -21.5926 |
|  | -5.9594 | -35.7535 |
|  | -0.3913 | -36.5208 |
| average | -1.28953 | -36.14971 |

FIG. 4

Procedures(repeat 5 times):

(1) Treat the SAW chip with protein G(10ug/mL) in 1x PBS overnight in a humidor at room temperature.

(2) Wash with PBST(0.1x) once.

(3) Load α-PAG(IDEXX, 2nd antibody detector) and keep for 1hour at room temperature.

(4) Wash with PBST(0.1x) once.

(5) Block with buffer B(0.1x) for 30~60min at room temperature.

(6) Load serum(1:5~1:20) to optimize the dilution as positive/negative experimental group.

Or Load 0.1xbuffer B as negative control group.

Sweep and data process:

(1) 5mV, 40~6MHz, 1s. Get Co as initial capacitance over frequency.

(2) 100mV, 100kHz, 60s. Get C as capacitance over time.

(3) 5mV, 40~6MHz, 1s. Get Cf as final capacitance over frequency.

(4) Calculate $dC/Co=(Cf-Co)/Co \times 1000$[‰/min] over frequency and $dC/dt$ under 100mV@kHz[‰/min].

FIG. 21

METHODS FOR DETECTING A BIOMARKER BY ALTERNATING CURRENT ELECTROKINETICS

CROSS-REFERENCE TO RELATED APPLICATIONS

This is a continuation in part of U.S. National Stage application Ser. No. 14/374,312, filed Jul. 24, 2014, which is based on International Application No. PCT/US2013/022447, filed Jan. 22, 2013, and claims the benefit of priority to U.S. Provisional Patent Application No. 61/591,713, filed Jan. 27, 2012, the entire disclosures of which are incorporated by reference herein.

STATEMENT OF GOVERNMENT SUPPORT

This invention was made with United States Government support under the National Science Foundation contract number ECS 0448896. The United States Government has certain rights in this invention.

FIELD OF THE INVENTION

The present invention generally relates to methods and related apparatus for detection of biomarkers in, for example, biological samples using alternating current electrokinetics (ACEK) for in-field (i.e., on-site, bed-side, laboratory-free) detection of many pathogens, diseases and physiological conditions or indicators thereof and, more particularly, to field detection of antibodies for diagnosis of bacterial diseases such as Johne's disease and mastitis in animals, antibodies for diagnosis of tuberculosis in animals and humans, D-Dimer for diagnosis of pulmonary embolism in animals and humans, small molecule (e.g., progesterone) for diagnosis of pregnancy, sugar (e.g., glucose) and enzyme (e.g., glucose oxidase for diagnosis of diabetes and other enzymes as an indicator of a heart attack by such methods and apparatus.

BACKGROUND

The phenomena of dielectrophoresis, alternating current (AC) electrothermal effect and AC electroosmosis, collectively referred to as alternating current (AC) electrokinetics (ACEK), are now being used to manipulate and separate particles on a cellular scale. Dielectrophoresis (DEP) involves the suspension of a dielectric particle in a non-uniform electric field. As will be discussed further herein, capacitive and impedance changes may be recognized from, for example, a two (or more) electrode array coated with a molecular probe (such as bacterial antigen) for substances under examination. If a polarized particle is suspended in such a field, an induced dipole will form across the particle and rotate or move in synchrony with the field. Furthermore, as will be depicted and discussed herein, the AC electrothermal and AC electroosmosis phenomena or effects will induce microscale flows around the electrodes, convecting particles/colloids/macromolecules to the electrodes for detection.

Interdigitated micro-electrodes or two closely spaced parallel plates are known and described, for example, in *Capacitive Microsystems for Biological Sensing*, V. Tsouti et al., *Biosensors and Biolelectronics*, 27, (2011), pp. 1-11. In simplified form, electrodes of a capacitance-type sensor may comprise two closely spaced parallel plates having particular spacing and thickness. A parallel connection of capacitors having two electrodes may be formed. It is well known that the sum of the individual capacitors in parallel comprises the capacitance of the parallel capacitors. While described as capacitors, no capacitor exhibits perfect capacitance without resistive and inductive components to create an impedance. Yet, the resistive and inductive components of such capacitive microsystems are less indicative of surface binding compared to the capacitive component. Such biosensors have been particularly developed and utilized, for example, in the detection of *Escherichia coli* and *salmonella*. Another electrode array is known for prostate specific antigen (PSA) testing for prostate cancer. Yet another prototype test integrated circuit has been developed for certain protein detection.

Johne's disease is caused by bacteria known as *Mycobacterium avium* subspecies *paratuberculosis*. Johne's disease affects wildlife and livestock. In livestock such as cattle or dairy cows, the disease causes reduction of milk production (dairy cows), weight loss and premature culling of clinically affected animals. In the United States alone, Johne's disease has been found in 68% of dairy herds and causes an estimated annual loss of $220 million to the U.S. dairy industry alone. Johne's disease is currently diagnosed in diagnostic laboratories using immunoassay or enzyme-linked immunosorbent assay (ELISA) or pathogen detection methods (bacterial culture or PCR indicative of infection or contamination).

*Mycobacterium bovis* causes bovine tuberculosis both in animals and humans. Despite progress towards eradication of bovine tuberculosis from U.S. livestock, states like Michigan and Minnesota continue to struggle with bovine tuberculosis in their wildlife and cattle operation. Mandatory testing of cattle costs $3.25 million per year in Minnesota alone. In the U.S., incidences of bovine tuberculosis cost more than $40 million in 2008-2009 for testing and treatment. Bovine tuberculosis in wild animals is currently tested by postmortem examination of gross lesion, bacterial culture, and skin test.

Human tuberculosis, caused by *Mycobacterium tuberculosis*, occurs in more than ten million people and, worldwide, is estimated to be responsible for the death of two million people annually. It is estimated that over one billion dollars is spent on diagnosis and evaluation of human tuberculosis worldwide each year. Human tuberculosis is currently diagnosed by radiographic imaging (conventional chest x-ray), smear microscopy, bacterial culture, or a tuberculin skin test.

Mastitis is a disease that results in inflammation of the mammary gland that is mostly caused by bacterial infections. The disease is the most common cause of death in adult dairy cattle. Indeed, it is estimated that 38% of all cows are affected with mastitis. Mastitis causes an estimated 1.7-2.0 billion USD annual economic loss to the U.S. dairy industry. Worldwide, it is the most costly disease affecting the dairy industry, incurring economic losses estimated at $50 billion/year (~£31 billion/year). *Escherichia coli* and *Streptococcus uberis* are common causative agents of bovine mastitis and are responsible for about 18% and 5% of the disease, respectively. Bacterial counts in milk of mastitis cow can reach $10^7$ bacteria/mL. A further indication of mastitis in lactating animals is somatic white blood cell count, which can be determined by mixing infected cow milk with a reagent and the amount of gel formed indicates a count of somatic cells and so an indication of mastitis. Detection and identification of the bacteria in fresh milk are critically important for treatment and control of the disease in dairy farms.

From U.S. Pat. Nos. 7,517,955 and 7,812,147 assigned to the University of Tennessee Research Foundation, a polypeptide, designated "*Streptococcus uberis* Adhesion Molecule" or SUAM, was developed by a team comprising Stephen P. Oliver et al. SUAM may be used diagnostically and therapeutically. The patents further describe an immune-fluorescence milk card-test and an agglutination/precipitation test that may be used "cow-side" for diagnosis as well as known ELISA testing which may require hours in a laboratory for results.

In the home and in the field, it would be beneficial if a laboratory on an integrated circuit (chip), as has been developed for other diseases, and related methodology may be available for rapid testing of wildlife, livestock, and humans for diseases and physiological conditions such as bacterial diseases including tuberculosis, Johne's disease, mastitis, and instances of heart attack among other diagnosis.

D-Dimer is an indicator of the degradation of a clot and, hence, is a predictor or indicator of a pulmonary embolism, deep venous thrombosis and the like. Clots are often fatal for example a clot that may form in a vein and return to the heart. It is desirable to have a lab-on-a-chip test for the detection of D-dimer.

High/low sugar content, for example, glucose of the blood and other bodily fluids is an indicator of hyper or hypo glycemia among other predictors of sugar related disease. A lab-on-a-chip test for sugar content may help patients and doctors determine such sugar related ease immediately and compete with existing methodology. Moreover, a possible industrial or commercial application is, for example, to test sugar content in beer.

Small molecule detection generally relates to any small molecule that may be a predictor of a disease of a condition. Specifically, it may, for example, be desirable to test for progesterone as an example of a condition such as pregnancy.

Enzymes are complexes produced, for example, in living cells of human organs or skeletal structures. Consequently, while ELISA testing is available, there is a need for a simple lab-on-a-chip test for enzyme level that can be an organ disease marker and accomplish in minutes what ELISA may require a formal laboratory and days to obtain results.

Another potential lab-on-a-chip application is in the testing of well water for coliform or *E. coli* bacteria in water rather than wait for a culture of other slow laboratory means for testing known in the art. Another bacteria requiring swabbing and testing is *Streptococcus* which is an indicator, for example, of strep throat.

Given the foregoing, what are needed are methods and related lab-on-a-chip apparatus that may provide for detection of bacterial and other infectious diseases, conditions via biomarkers or even for use in commercial applications, for example, using ACEK phenomena.

SUMMARY

This summary is provided to introduce a selection of concepts. These concepts are further described below in the Detailed Description. This summary is not intended to identify key features or essential features of the claimed subject matter, nor is this summary intended as an aid in determining the scope of the claimed subject matter.

The present invention meets the above-identified needs by providing an apparatus such as an off-the-shelf surface acoustic wave resonator having an electrode array or a specially fabricated electrode array. The electrode arrays of each may comprise a lab-on-a-chip for detection of pathogens, diseases, and physiological conditions. Parameters associated with the fabricated electrode array to investigate improving the limits of detection of pathogen, disease, or a physical condition. For white somatic cell count for mastitis, a further special array has been designed comprising first and second overlaying electrode meshes (first and second network grids) of different sized openings as will be further defined herein in connection with a discussion of FIGS. 19A-19D. Moreover, a generic method will be described for each of detection of Johne's disease, tuberculosis, pathogen detection (mastitis), somatic cell detection (mastitis), protein detection (pregnancy), small molecule, and D-dimer. The described electrode array platform is a platform technology that will help any detection/assay that is based on a heterogeneous reaction. It has been well documented that impedance sensing can be used for immunodiagnosis, DNA assay, and enzymatic sensing. The disclosed platform improves on heterogeneous based impedance sensing on a whole. Impedance biosensors applicable to the disclosed platform include the three types introduced above (i.e., biosensors for detection of antigen/antibody, DNA, RNA (nucleic acid), and enzyme) and further include glucose as an example of a sugar, D-dimer as one example of a protein biomarker, progesterone as one example of a small molecule and *S. uberis* as an example of microorganisms including bacteria and cells.

In one embodiment, the present invention comprises an interdigitated electrode array such as an electrode array of a conventional surface acoustic wave (SAW) resonator at 433.92 MHz available from AVX Corporation, PARS 433.92, having interlaced electrodes spaced at approximately 2 µm apart, i.e., one to three micron width of each electrode finger and one to three micron separation from one another. An associated method of preparing the lab-on-a-chip comprises coating a surface of the electrode array portions of the integrated circuits with bacterial antigen. According to tests performed thus far, the bacterial antigens may be an extract of the causative agent of Johne's disease or tuberculosis. For pathogen detection for mastitis and biomarker (pregnancy-associated glycoprotein (PAG)) detection for pregnancy, antibody against the pathogen or PAG may be directly or indirectly (e.g., via Protein G) coated on the electrode surface to capture the pathogen or protein. Any uncoated surface is blocked with a blocking reagent. For detection, a serum sample or suspension of pathogens is loaded to the coated and blocked lab-on-a-chip. Antibodies, generally biomarkers, or pathogens bind to the bacterial antigen or to the anti-pathogen antibody or to the anti-biomarker antibody when an electrical signal of predetermined magnitude and frequency is applied to the electrodes. Such antibody/pathogen, generally, biomarker, binding translates into a change in capacitance or impedance value over time on the order of one to six minutes, depending on the condition sought to be detected by their antibody/pathogen/biomarker when compared with unaffected samples.

A biomarker, or biological marker, as used herein, as a generic description of what substance is applied to the electrode array is, in general, a substance used as an indicator of a biological state, which may indicate infectious disease or a physical condition such as pregnancy or clotting (onset of an embolism). Progesterone may be detected as an example of small molecule detection. It is a characteristic that is objectively measured and evaluated as an indicator of normal biological processes, pathogenic processes, abnormal biological processes or pharmacologic responses to a therapeutic intervention. It can also be a substance whose detection indicates a particular disease state, for example, the presence of an antibody may indicate an infection. More specifically, a concentration of a biomarker may indicate the risk or progression of a disease, or with the susceptibility of the disease to a given treatment. For example, pregnancy-associated glycoprotein, D-dimer, and glucose are indicators of, for example, pregnancy, embolism, and diabetes (or other sugar related diseases), respectively. A binding assay as used herein refers to the binding, affinity, attraction, or actual adherence of one molecule to another as may be seen represented in FIG. 3B and FIG. 10, e.g., a binding assay is a specific assay that measures the amount of binding or affinity between two molecules.

In another embodiment, rather than detecting a change in capacitance or impedance value over time resulting from a biomarker binding to the electrodes, the lab-on-a-chip may detect a change in interfacial capacitance due a change of conductivity of the sample solution resulting from enzymatic redox (reduction-oxidation) reactions close to the surface of the electrodes. The electrode array is functionalized/coated with either linker molecules specific to diagnostic redox enzymes or redox enzymes themselves. A low AC voltage signal is applied to the electrode array to induce ACEK effects that create convection of target molecules (e.g., enzymes, substrates, and/or probes) towards the surface of the electrode array, promoting redox reaction catalyzed by enzymes captured by the linker molecules or the immobilized enzymes. The redox reaction specific to the enzyme-substrate pair may be detected by measuring the change in interfacial capacitance at the surface of the electrode array.

In an alternative embodiment, an array of electrodes has been fabricated in a configuration of 25-μm wide and spaced electrodes having approximately 5-μm contacts on a silicon substrate or wafer. In this embodiment, the parallel interlaced fingers may comprise an approximately 25 micron finger, an approximately five micron space, an approximately five micron finger and an approximately 25 micron space to form an interlaced pattern for a two electrode array on the silicon substrate. This fabricated array resulted in improved results over the commercially available array from the known SAW resonator. Different fabricated arrays have been investigated to determine the limits of detection of such an array, for example, a combination of symmetric and asymmetric interdigitated electrodes to detect even lower concentrations of a biomarker binding. Moreover, in a use of the present invention for detection of D-dimer, the use of a Polypyrrole (PPy) coated electrode was tested and compared with results using no coating of this array. Also, during a small molecule detection application of the invention (for example, progesterone detection), the impact of applying a 3-aminopropyl-triethoxysilane (APTES) coating was tested and results showed that capacitance change rates over time rose with APTES compared with testing detection without APTES. Finally, a special mesh (grid) electrode has been developed for the detection of somatic cells in a biological sample as an indicator of mastitis and may likewise be used for other detection as well as will be further discussed herein with reference to FIGS. 19A-19D.

In one embodiment discussed herein, a plurality of electrode arrays may be distributed on the surface of the same chip so that multiple samples may be multiplexed, and digital data for capacitance/impedance over time collected for all deposited samples simultaneously. A four-inch diameter (ten-centimeter) substrate may be used or other suitable size as small as five millimeters or smaller (as long as an electrode pair may be accommodated). As many as twenty or more biological samples may be tested simultaneously via twenty or more electrode arrays formed on the same substrate.

In further embodiments, electrode meshes (grid networks) may be overlaid on a substrate (for example, configured as a capacitor as will be discussed with reference to FIGS. 19A-19D) or wide interdigitated electrodes used with narrow electrodes as will be discussed further herein. The overlaid electrode meshes/grids (FIGS. 19A-19D) may be used for somatic cell count in mastitis stricken lactating animals.

Other electrode configurations may include pin-line coplanar electrodes and face-to-face patterned electrodes. Any microelectrode designs that produce non-uniform electric fields may be implemented as an ACEK-based impedimetric lab-on-a-chip. Any uniform, conductive polymer may be used as a coating to improve detection in some embodiments while Polypyrrole (PPy) was used by way of example. In an alternative embodiment, a coating comprising a nanostructured material may be applied to improve detection. Examples of nano-structured materials include zinc oxide (ZnO), nanotube, and graphene among other nano-structured material coatings known in the art. In yet another embodiment, detection may be amplified by conjugating sample analytes with nano- to micro-size labeling particles and then loading the conjugated sample onto the electrodes. For example, the labeling particles may be latex beads, magnetic beads, or microorganisms such as virus, bacteria.

Either a commercially available, a custom micro-fabricated or other embodiments of such electrode arrays may be fabricated that may be pre-coated with a bacterial antigen or antibody against targeted pathogen or protein and blocked so as to comprise a lab-on-a-chip for field use, saving time and expense associated with transmitting samples to laboratories, for example, for enzyme-linked immunosorbent assay (ELISA) testing or other laboratory testing. In bacteria detection, for example, *streptococcus* in saliva or coliform or *E. Coli* in well water or even *salmonella* sampling in food, tests may be performed in five minutes where conventional testing may require overnight culture growth and the like, i.e., detection may be faster, more efficient, and cost less money. While milk is described as a human or animal testing vehicle, other body fluids such as sweat, saliva, blood, and urine may be tested for worthwhile purpose. Applications may include five-minute testing of saliva for *streptococcus*, of beer for sugar content, or of blood or sweat or other body fluids for evidence of D-dimer and blood clotting.

In principle, the system can detect analytes other than antibody, pathogen (e.g., antigen of pathogen, biomarker proteins associated with disease, infection, contamination or physiological conditions), protein, small molecules, types of sugar such as glucose and enzyme level and therefore may be used for diagnosis of various diseases, proteins and physiological conditions such as pregnancy, blood clotting, recent heart attack and other conditions of animals and humans or dangers to animals or humans (such as an application for well water testing) as will be described herein. The lab-on-a-chip embodiment and coating/blocking tests discussed herein may find application in food safety, for example, in testing meats, milk and dairy products, water and the like as well as use in homeland security applications and commercial applications such as testing for sugar level in beer. Such applications of the lab-on-a-chip and related methods may include rapid testing and diagnosis at border crossings for infectious diseases in humans and animals and in receipt of imported food products at ports or airports.

Further features and advantages of the present invention, as well as the structure and operation of various aspects of the present invention, are described in detail below with reference to the accompanying drawings.

BRIEF DESCRIPTION OF THE DRAWINGS

The features and advantages of the present invention will become more apparent from the detailed description set forth below when taken in conjunction with the drawings in which like reference numbers indicate identical or functionally similar elements.

FIG. 4 provides blind test results for Johne's disease for twenty serum samples, ten testing negative and ten testing positive for the disease using the exemplary electrode array of FIG. 1.

FIG. 20B investigates levels of concentration of sample 4118 versus no somatic cells to show that 100 dilute sample 4118 may detect mastitis versus no cell; FIG. 20C shows count of somatic cells (somatic cell count or SCC) over a five minute test period versus change in capacitance versus change in time to show accuracy of experimental results.

FIG. 21 illustrates the steps of a process of preparing a SAW electrode array of FIG. 1 for a pregnancy test utilizing a coating of α-PAG (anti-PAG antibody) for pregnancy detection.

DETAILED DESCRIPTION

The present invention is directed to systems, methods and computer program products that provide exemplary electrode arrays and methods associated with those arrays for the detection of pathogens, diseases and physiological conditions, in particular, pregnancy, tuberculosis, Johne's disease and mastitis among other conditions including but not limited to testing for bacteria in well water, detection of glucose, detection of enzyme levels, detection of D-dimer and small molecule detection as exemplified by progesterone detection. An example of a preferred topology for an electrode array is provided in FIG. 9A, 9B while a commercial array may be used as per FIG. 1A, 1B. In either case, a method is disclosed according to FIG. 2A whereby incidences of tuberculosis, Johne's disease and mastitis among other bacterial diseases may be distinguished utilizing the electrode arrays of FIGS. 1 and 9.

Figure 2A:
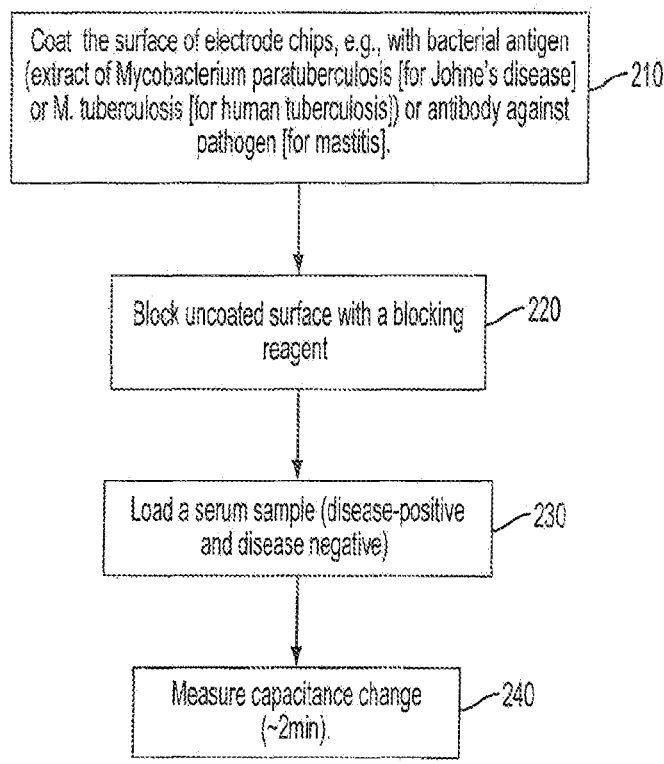
FIG. 2A is an exemplary flow chart diagram of a detection method according to the present invention.

Detection tests will be first discussed which have been conducted using an electrode array from a commercially available SAW resonator integrated circuit, namely, a PARS 433.92 SAW resonator available from AVX Corporation whereby the electrode array thereof was coated and treated according to the process of FIG. 2A to form a detection kit including a signal generator, microcontroller and capacitance/impedance display read-out. Tests were conducted using Johne's disease serum samples and tests were also conducted using cattle, human and wildlife (badger) tuberculosis serum samples. Also, tests were conducted to detect pathogen (*Streptococcus uberis*) that causes mastitis of two types, pathogen detection and abnormal white cell detection. The limits of detection were tested by varying the concentrations of antibody. Further, tests were conducted to detect biomarker (PAG) of pregnancy in ruminants. As reported in Li, S. et al. (including inventor Jie (Jayne) Wu), Biosensors and Bioelectronics (2012), "Dielectrophoretic responses of DNA and fluorophore in physiological solution of impedimetric characterization," incorporated herein as to its entire contents, this same SAW resonator chip was successfully used to differentiate DNA. Moreover, the successful repeatability of the detection tests will be discussed.

After utilizing the electrode array that is commercially available, first and second preferred microfabricated electrode arrays were designed, constructed and similarly tested with improved results. A discussion of the improved electrode arrays (FIGS. 9 and 23) and of the improved results follows a discussion of the use of the electrode array taken from the commercially available SAW resonator. First and second overlaid electrode meshes/grid networks configured as a capacitor will also be discussed with reference to FIGS. 19A-19D.

Figure 1A:
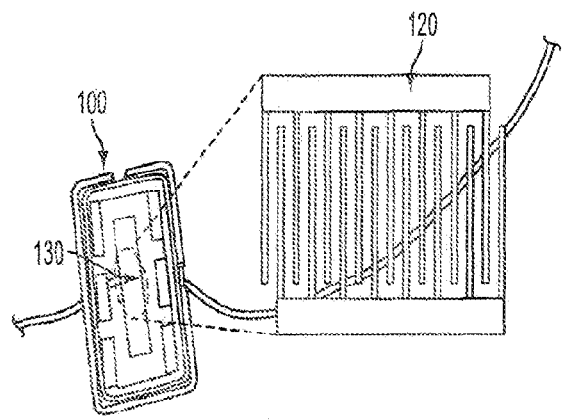
FIG. 1A is, in part, a photograph of a conventional SAW resonator chip having an associated interlaced electrode portion used as an electrode array embodiment and coated to provide for detection of Johne's disease and tuberculosis and further shows a blow-up diagram of the exemplary electrode array portion.
Figure 1B:
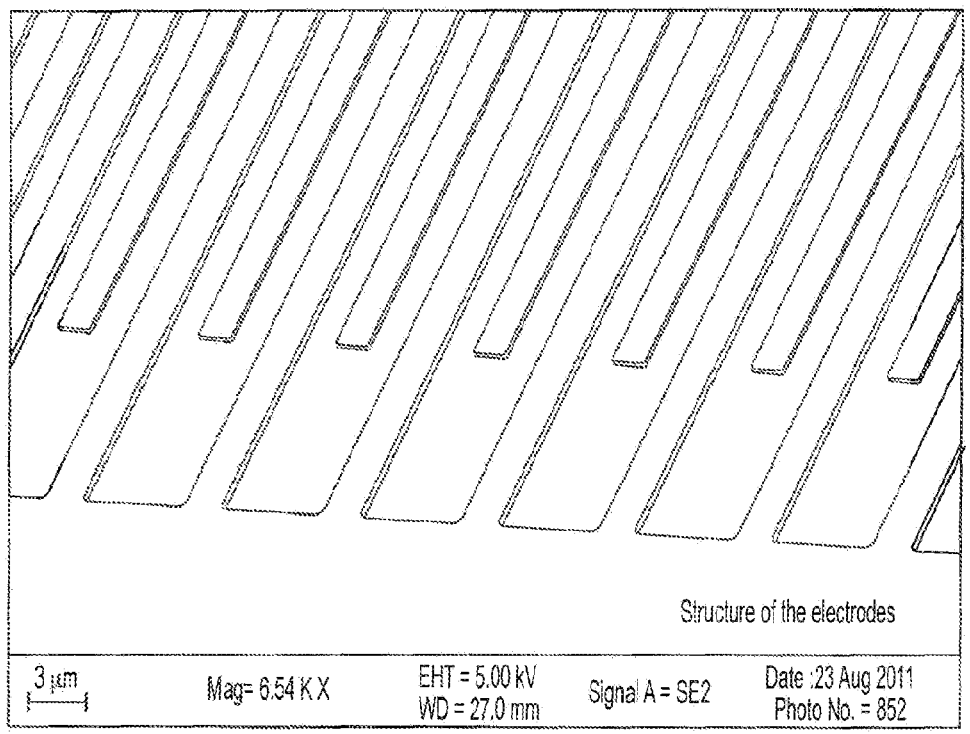
FIG. 1B is a micrograph showing a three micron scale where the structure of the electrodes of the conventional SAW chip may be viewed in perspective.

Referring now to FIG. 1A, there is shown a conventional, commercially available PARS 433.92 surface acoustic wave (SAW) resonator integrated circuit exposed in top view to show an electrode array portion 130 used according to FIG. 2A. In blow-up form, the electrode array appears as electrode array 120 as comprising a plurality of uniformly spaced fingers from first and second parallel electrode conductors. The structure of the electrode array may be better seen in the micrograph of FIG. 1B where each conductor (of aluminum) resides on a quartz/glass substrate. As will be further discussed herein, other conductive metals and substrates known in the art may be used to construct suitable electrode arrays. Each finger appears to have the same width, between 0.5 and 100 microns (for example, between 1 and 3 microns), or 1.7 microns in particular and has the same spacing or separation from one another, in a range of 0.5 and 100 microns, also, preferably, between 1.0 and 3 microns, or about 1.6 microns in spacing. A predetermined voltage in a range, for example, between approximately 5 mVrms and 10 Vrms (preferably between 10 mVrms and 1 Vrms) or, for example, between 100 and 500 mVrms is applied, for example, at a predetermined frequency in a range, for example, between as low as 20 Hz (preferably, 1 kHz) and 5 MHz and 1 kHz to 200 kHz in particular for approximately one to ten minutes, for example, two to three minutes, to induce ACEK effects.

To assemble a complete system, one may incorporates a board-level signal generator with the electrode array (for example, to generate a 100 mv, 100 kHz signal once a serum sample is deposited, an impedance or capacitance read-out device, a microcontroller as an intelligent interface to the impedance/capacitance readout and a display read-out. As determined from tests described below, the predetermined value of signal applied may range from 5 mVrms to ten Vrms (preferably 10 mVrms to one Vrms) and at a frequency between 20 Hz (preferably 1 kHz) and 5 MHz.

Figure 10:
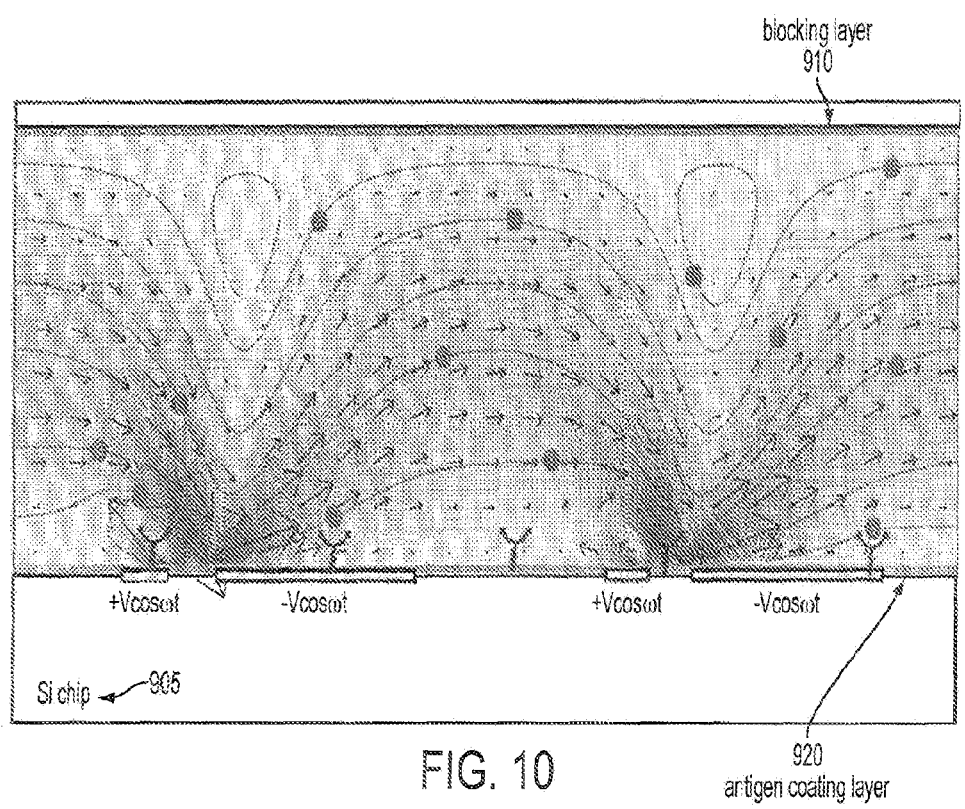
FIG. 10 provides a drawing similar to FIG. 3B showing how the electrode array may provide improved binding results between an antigen coating layer and a blocking layer, taking advantage of convection by long-range AC electrothermal flows.

Construction of a detection test kit and the application of serum thereto is provided by the flowchart of FIG. 2A. In a first step 210, one coats the surface of an exemplary electrode array or integrated circuit array portion with a bacterial antigen (for example, an extract of *Mycobacterium avium* subspecies *paratuberculosis* for Johne's disease or *M. tuberculosis* for human tuberculosis, antibody against PAG for pregnancy, or antibody against pathogen for mastitis). At step 220, one blocks the surface with a blocking buffer reagent. One such blocking agent that may be used comprises a phosphate-buffered saline (pH 7.0) containing 0.05% Tween20 and 10% SuperBlock blocking buffer available from Thermo Fisher Scientific of Rockford, Ill. The pH level may be, for example, between 2.0 and 11.0 with 7.0 preferred. Other blocking agents known in the art may be used. One may wash the uncoated surface with a wash such as phosphate buffered saline Tween (PB ST) or other suitable wash. The electrode array apparatus may also take the form, for example, as seen in FIG. 10 in cross-section: a silicon (Si) substrate or wafer is provided with an electrode array deposited by conventional evaporation/sputtering in gold/titanium, gold/chromium, aluminum, copper, silver or other conductive material with a blocking layer on top and an antigen coating layer between. The electrode array chip is connected to a signal generator chip, a microcontroller and a display read-out before sample loading in one embodiment. For bio-particles with pronounced DEP responses (i.e., obvious attraction or repulsion to electrodes by a selected electrical signal, such as DEP responses of cells), by the choice of electrical signal frequency and magnitude, selective trapping/detection and improved selectivity may be realized. In some cases, surface functionalization may not be needed, and the electrodes can be reused without washing, etc.

Next, a serum sample (a biomarker) is loaded at step 230, for example, by dropping from a pipette onto the coated surface of the electrode operating at a given millivolt level and frequency signal as discussed below. In testing, blind and other tests were conducted which would result in disease positive or disease negative results. As discussed herein, at step 240 a change in capacitance (or a change in impedance) results over time as antibodies in the serum bind with the coated antigen layer under test with the given signal. The serum may be formed, for example, from a selected body fluid, for example, milk from lactating female animals, blood, saliva, sweat and urine, depending on the application of the impedimetric sensor (lab-on-a-chip).

Once the electrode array chip is used, it may be washed and be reused with the same signal generator, microcontroller and display. The washing may, for example, comprise use of an avidin (glycoprotein)-biotin interaction or a biotin/streptaviden interaction in conjunction with a sodium hydroxide (NaOH) solution or a potassium hydrochloride/sodium hydroxide (KOH/NaOH) solution or other washing solution known in the art to clean off the antigen/coating so the electrode array may be reused.

In commercial production, it is expected that an integrated circuit may be distributed with an on-chip signal generator and electrode array exposed with an antigen coating already applied and blocked with the reagent. Alternatively, antigen and coating may be applied on site, blocked, the lab-on-a-chip used once, washed and then reused until it becomes ineffective. In one embodiment, the electrode array may comprise a separate chip that may be easily reused and replaced, for example, if its effectiveness decays after multiple uses and washings. As will be discussed further herein with respect to FIG. 2B, a system may comprise a microcontroller, a multiple sample array, a multiplexer, a signal generator and a connector to a personal computer or communication devices for communication of results to remote laboratories or disease centers or other remote facilities. In this example, the integrated circuit will be ready for loading of a plurality of samples which may be tested simultaneously. As many, for example, as twenty samples may be tested simultaneously with a like number of electrode arrays deposited on the same substrate. The entire system may be constructed as portable and useable in the field (not at a laboratory) such as at a dairy or cattle farm or even in the home. Results are available in minutes rather than hours as with a laboratory ELISA (enzyme-linked immunosorbent assay) test. Also, from the testing conducted thus far, only approximately two micro-liters of serum sample is required at a given concentration as will be discussed further herein to provide satisfactory detection. Consequently, many samples may be tested simultaneously on the same lab-on-a-chip. Such an amount of serum can be readily obtained from a human or animal body fluid (milk, blood, urine, saliva, . . . ) sample without any need for using a centrifuge.

Figure 2B:
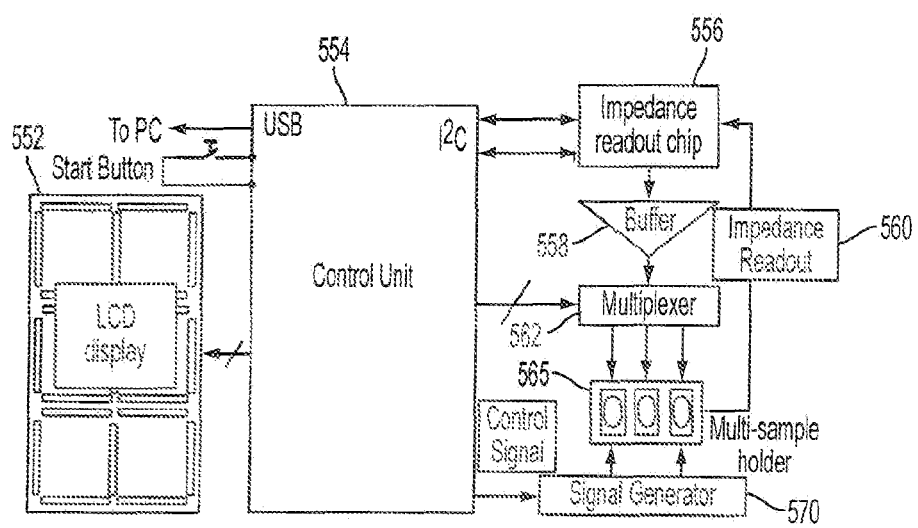
FIG. 2B is an exemplary circuit block diagram of a multiplex electrode array in combination with a signal generator, a controller and display for field detection of physiological conditions and infectious diseases such as the bacterial diseases Johne's disease and tuberculosis.

FIG. 2B is an exemplary circuit block diagram of a multiplex electrode array in combination with a signal generator, a controller (computer processor and memory) and display for field detection of physiological conditions and infectious diseases such as the bacterial diseases Johne's disease and tuberculosis. In particular, the apparatus of FIG. 2B comprises a multi-sample holder 565 which may comprise a plurality of electrode arrays of FIG. 1A or a lab-on-a-chip as per FIG. 9 where there may be multiple electrode arrays for receiving multiple biological specimens for testing simultaneously (three shown). A signal generator 570 is shown connecting the control unit, preferably a microcontroller 554 known in the art including on-board data memory (not shown) to the multi-sample holder 565. The line from controller 554 to signal generator 570 represents a control signal line indicating a predetermined signal or voltage level and a predetermined frequency so that signal generator 570, in response, will output a signal according to a user signal selection. The user selected signal values of voltage and frequency may be input from a personal computer (including a keyboard) or other intelligent device such as a pad computer or intelligent telephone and stored in microcontroller memory or external memory not shown. Microcontroller 554 also connects to multiplexer 562 which is connected between impedance readout circuit 556 and multi-sample holder 565 via a buffer circuit 558.

On the left side of FIG. 2B, there are shown a connection to a personal computer, for example, a USB port, or to a storage memory card. The personal computer may receive data from microcontroller 554 and be used to retransmit the data via a communications port and network to disease control agencies, an external laboratory or anywhere that a user may wish to send the data. A start button is used to start a testing or multiple simultaneous sampling of tests, for example, once biological samples are loaded in the multi-sample holder 565. Detection/diagnosis may be performed in three steps. Step 1: When start is pushed, a control signal is sent to the controller 554 to activate multiplexer 562 and impedance readout chip 556 to obtain multiplex readouts via the impedance readout line from the sample holder 565 to the impedance chip 556. The impedance chip 556 reports the capacitance/impedance value as a signal or plurality of signals, one for each sample, to controller 554, setting the initial capacitance/impedance values for the electrode array(s). Step 2: The controller 554 activates signal generator 570 to apply a signal of selected magnitude and frequency to sample holder 565 for a predetermined period (for example, less than ten minutes), which is meant to induce ACEK effects to enhance the deposition of macromolecules/bioparticles onto the electrode surfaces. Step 3: The controller 554 again activates multiplexer 562 and impedance readout chip 556 to obtain multiplex readouts via the impedance readout line from the sample holder 565 to the impedance chip 556, which provide the end state of capacitance/impedance values after the predetermined period lapses. The impedance chip 556 reports the capacitance/impedance value as a signal or plurality of signals, one for each sample, to controller 554. An LCD or other display 552 may provide a read-out of sample data, for example, in capacitance or impedance value at pre-selected time intervals over the predetermined period for the particular application of the lab-on-a-chip. These periodic values may be temporarily stored in memory of microcontroller 554 (not shown) along with control. The personal computer may be used to provide a graphical indication of capacitance or impedance change over time in comparison with control or other concentrations and the like as per the several figures provided herein.

Figure 2C:
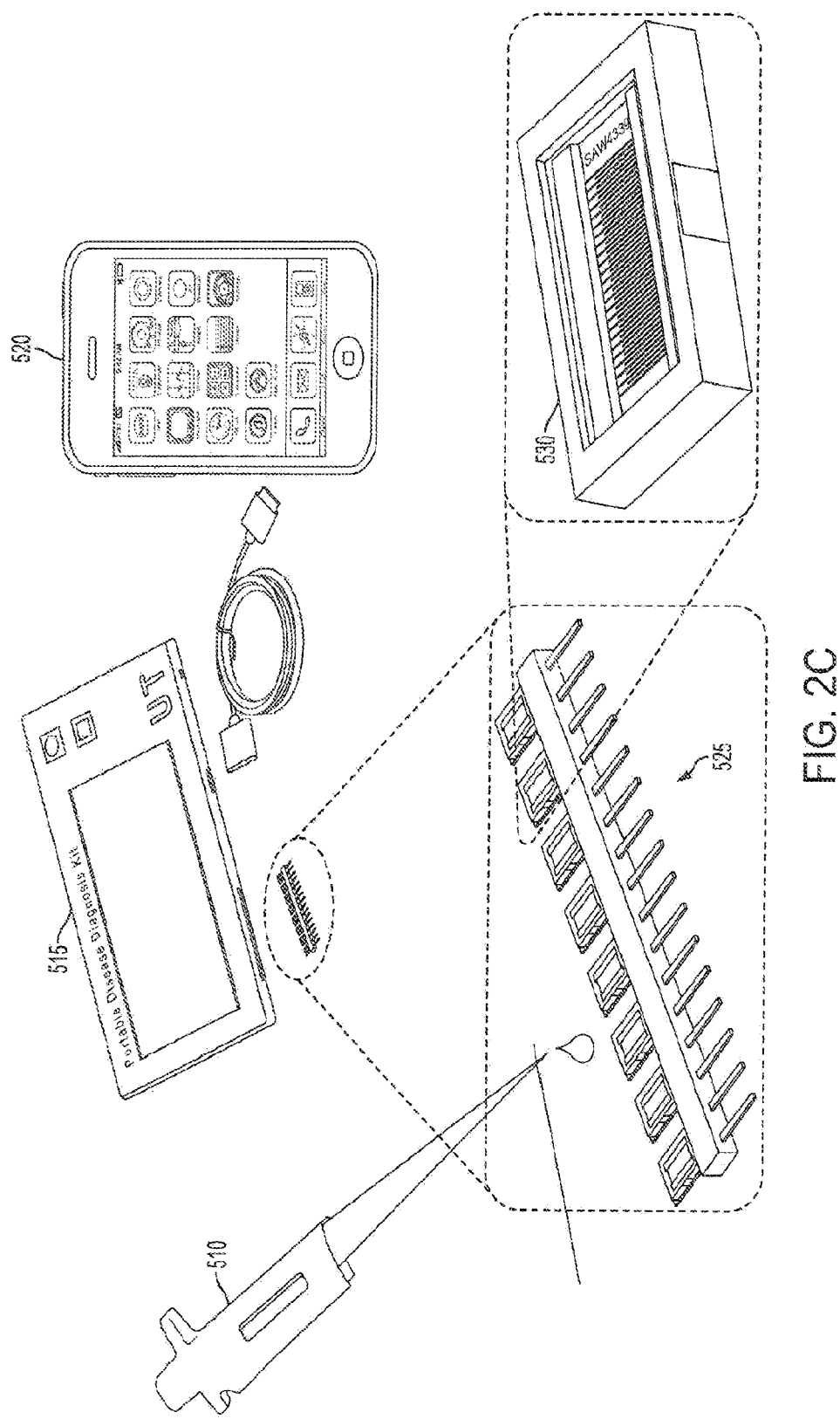
FIG. 2C shows a prototype portable disease diagnosis kit, a pipette for dropping samples, an interconnector to intelligent telecommunications apparatus, and a plug-in connector for a plurality of electrode arrays (eight shown).

Referring now to FIG. 2C, there is shown a complete kit for a lab-on-a-chip embodiment comprising, for example, pipette 510 for dropping blood/milk/saliva/urine or other biological sample on to an array 530, which may be one of, for example, eight arrays that may be attached via an interconnector 525 to a slot of the kit 515. The kit 515 may connect via standard connector cable to a port of an intelligent telephone 520 for remote transmittal of data.

Figure 2D:
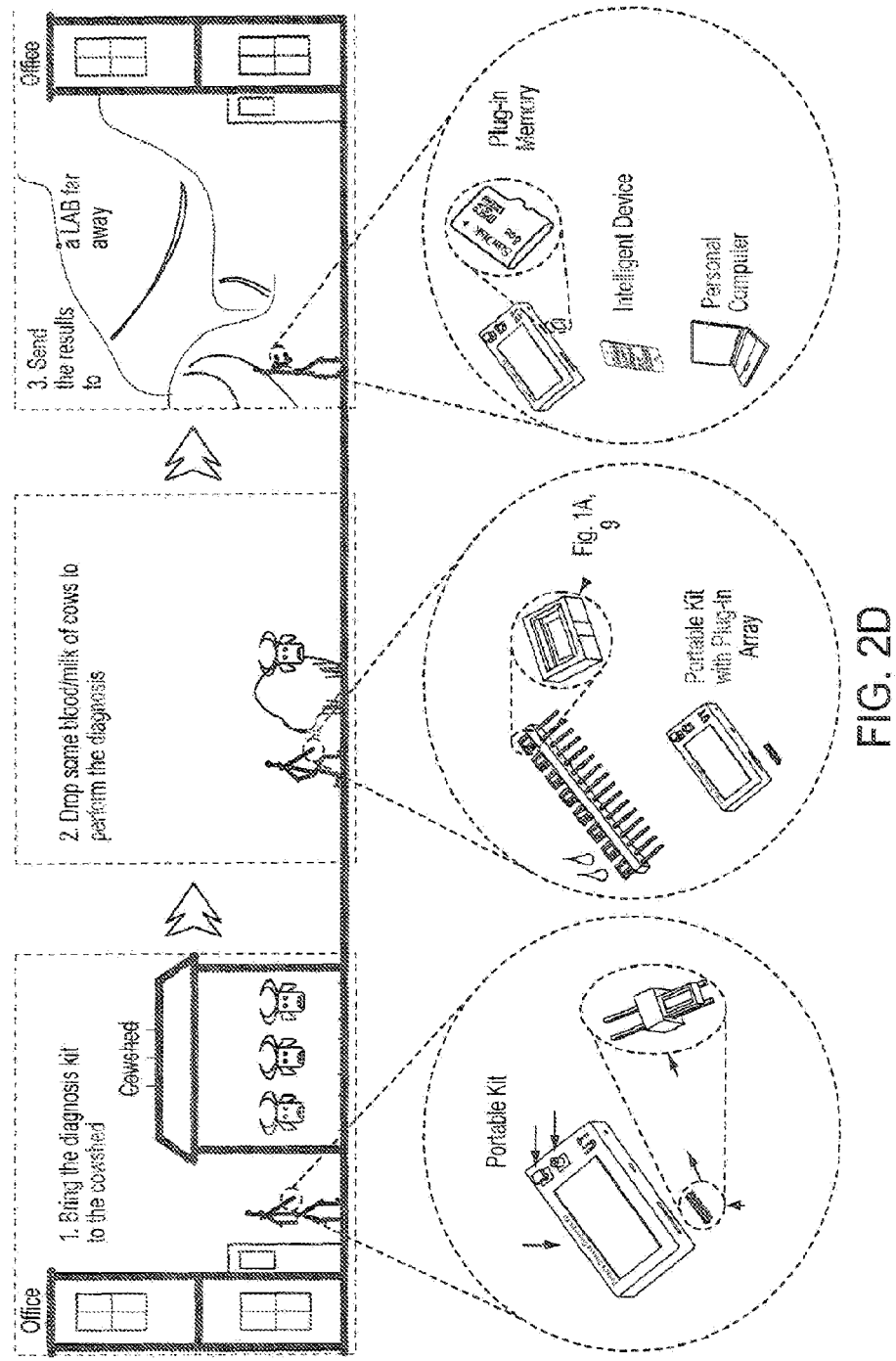
FIG. 2D shows an exemplary on-site process for obtaining and transmitting on-site detection/diagnosis and potentially sending results to disease control centers/laboratories and the like via an intelligent device/personal computer or storing results locally on a plug-in memory.

Per FIG. 2D, there is shown an exemplary farm application where a diagnostician takes the kit of FIG. 2C to a cowshed, drops some blood/milk/saliva/urine or other biological sample on a pre-coated surface of an array of FIG. 1A, 9 and then may store the data locally on an exemplary plug-in memory or use an intelligent device 520 or personal computer for data analysis or remote transmission to a laboratory or disease control center or other remote location.

Figure 3A:
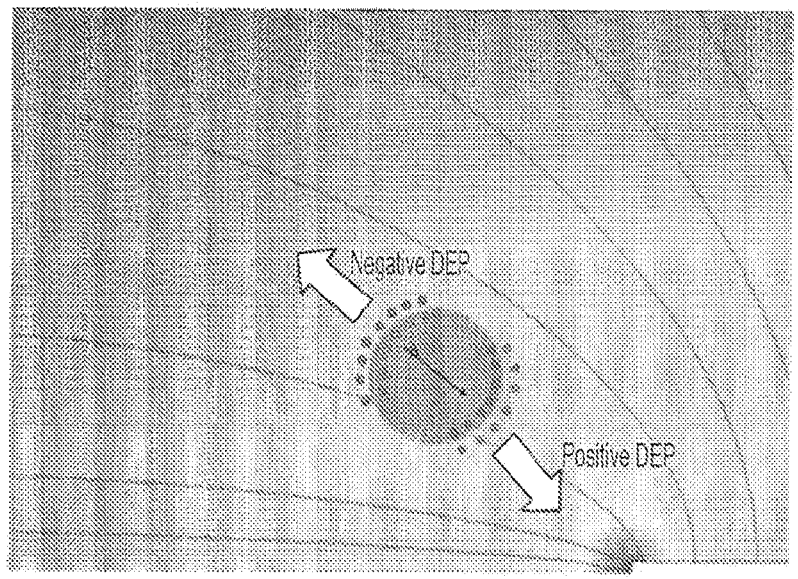
FIG. 3A shows the phenomenon of Dielectrophoresis (DEP) as applied to a molecule caught in an electric field above an electrode array in miniature for one such molecule.
Figure 3B:
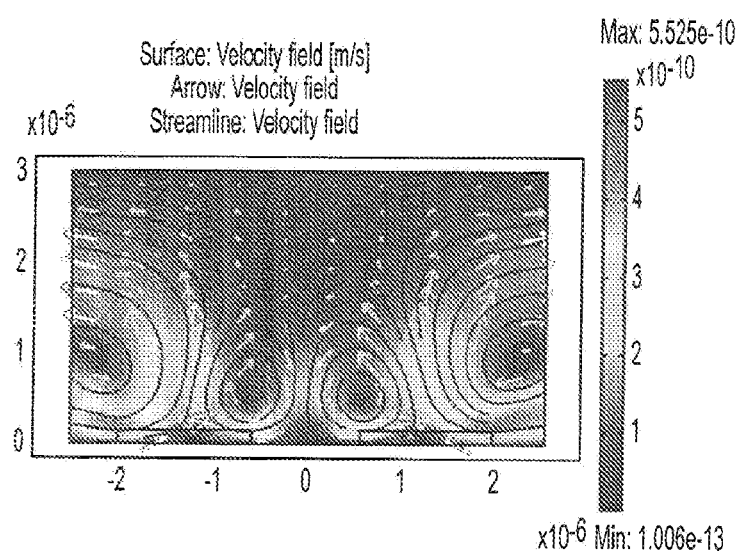
FIG. 3B provides an expanded view for an exemplary electrode array showing exaggerated rotation and directional forces applied such as those caused by an exemplary conventional electrode array of the electrode array of FIG. 1.

Referring briefly to FIG. 3A, negative and positive dielectrophoresis is shown by way of example acting on a molecule acting within an electric field caused by the applied electrical signal at a selected voltage and selected frequency. Referring now to FIG. 3B which shows AC electrokinetics in larger scale and with reference to a coated electrode array of a given geometry, molecules are shown at a surface velocity field in meters per second, the arrows and streamlines showing the velocity fields from the phenomenon.

Example 1—Johne's Disease

Referring now to FIG. 4, there are shown blind test results for Johne's disease comprising twenty samples, ten negative and ten positive, with the change rate in capacitance per minute shown. The minimum negative result had a value of −8.4539 and a maximum result of 8.2321% change in capacitance per minute. The positive test results show a marked difference with a minimum of −15.0843 and a maximum negative of −65.0035% change in capacitance per minute. There is a clear demarcation between a positive and a negative test at approximately −11%. The average is also shown for negative at −1.28953 compared with −36.14971, again showing a clear demarcation line between positive detection and negative testing. Blind tests for Johne's disease were even run by a different student performing tests of twenty samples with similar results: −5 to +5% per minute for negative versus −20 to −30% per minute for positive detection.

Figure 5A:
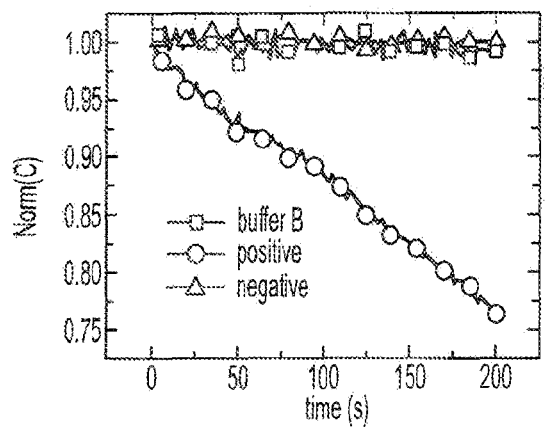
FIG. 5A provides a graph of normalized capacitance change of positive, negative sera for diagnosis of Johne's disease, with a buffer solution B as a control sample (1:10 antigen and 1:20 serum).
Figure 5B:
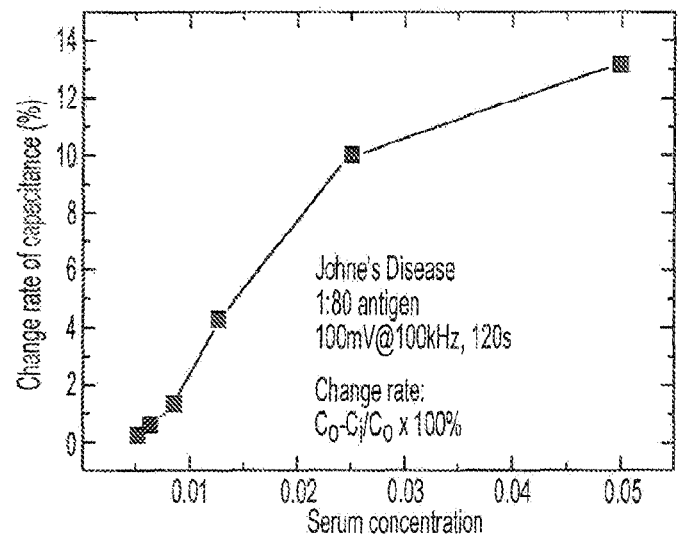
FIG. 5B is graph of serum concentration versus change rate of capacitance for Johne's disease 1:80 antigen.
Figure 5C:
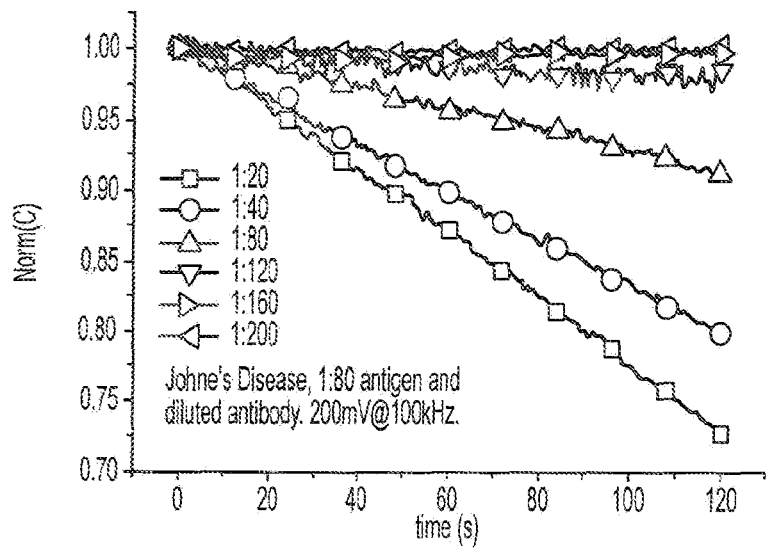
FIG. 5C is a graph of normalized capacitance over time in seconds for Johne's disease, 1:80 antigen and diluted antibody showing different linear results from a concentration range of 1:20 to 1:80.
Figure 5D:
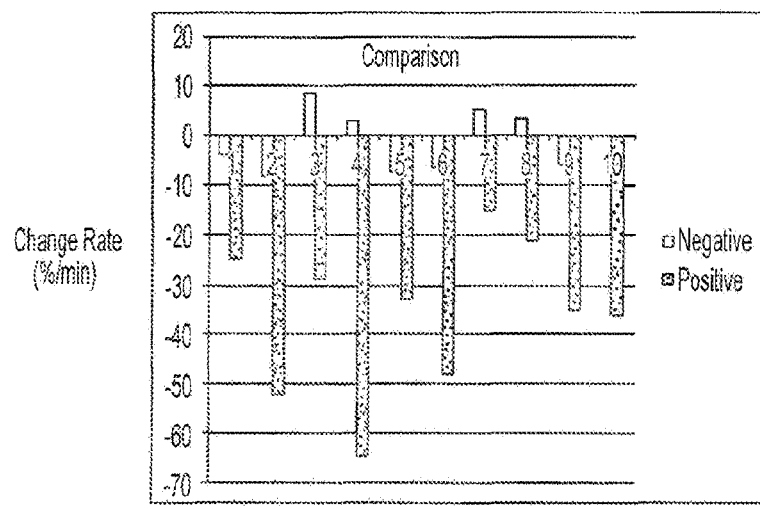
FIG. 5D provides a linear bar graph showing negative test results versus positive test detection, capacitive change rates for Johne's disease sera in % per minute versus the ten negative and positive results showing that Johne's disease detection results.

Referring now to FIG. 5A, there is shown a graph of normalized capacitance change of positive, negative sera for diagnosis of Johne's disease, with the buffer solution as the control sample (1:10 antigen and 1:20 antibody serum concentrations). The data was taken with an electrical signal applied to the electrode array at a selected magnitude of 500 mVrms and a selected frequency of 100 kHz. The duration of the tests is shown as running for 200 seconds, or just over three minutes. Test results (negative/positive) compared to control may be seen in about one minute or less compared with laboratory testing. FIG. 5C is similar. What is shown in FIG. 5C is that the serum concentrations may be varied from 1:1 to 1:80 without the measured capacitance/impedance over time as displayed in graphical form running into a control level. Concentrations of 1:120 to 1:200 are too weak to distinguish from control. FIG. 5B is a graph of serum concentration versus the % change rate of capacitance for Johne's disease at 1:80 and an applied signal of 100 mV at 100 kHz frequency for the predetermined test period, in this application, approximately 120 seconds or two minutes with the lab-on-a-chip of FIG. 1. Improved results are obtained from the lab-on-a-chip of FIG. 8 as will be discussed herein. FIG. 5D provides a linear bar graph showing negative test results versus positive test detection, capacitive change rates for Johne's disease sera in % change per minute versus the ten negative and positive results showing that Johne's disease detection results with clear threshold analysis.

Chip to chip reproducibility was tested by using the same test sample on five different coated electrodes. All five coated chip samples tested at a similar capacitive change rate for the same serum sample, between −20% per minute and -28% per minute. Serum to serum reproducibility was also tested using different serum samples for Johne's disease. The ten positive samples were tested on ten chips and the range in results was between −20 and -28% change in capacitance per minute.

Example 2—Tuberculosis

Eleven human tuberculosis samples were tested via the method of FIG. 2, six positives and five negatives. Each sample was tested twice. Sample 1 exhibited a change in capacitance of 39.0679% over time in a first test and the second test of the same sample at 14.3615% for an average value of 26.7147% resulting in a conclusion of a positive test for disease. A value of 25 was determined to be an appropriate threshold. Other average positive results included 42.89935, 45.7834, 71.02315 and 92.9081. These compare with negative average results less than the 25 threshold of 21.95305, 21.12935, 11.1021, 9.37895 and 8.49295.

Figure 6:
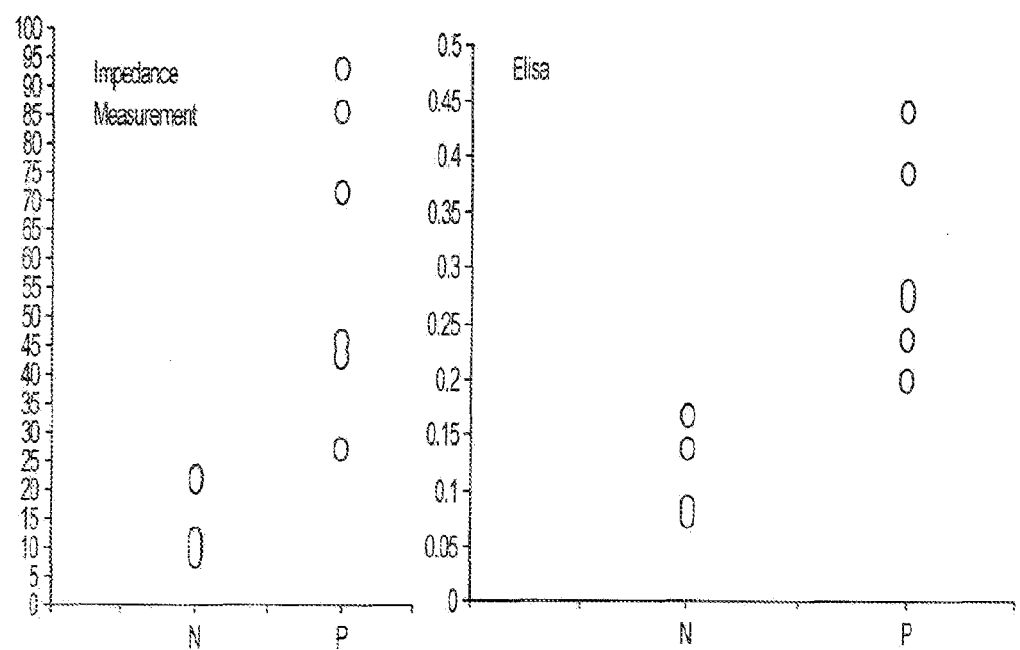
FIG. 6 provides a comparison between the method of the present invention for change in impedance and the widely used ELISA laboratory method for detection of human tuberculosis demonstrating similar results for negative and positive testing.

Referring to FIG. 6, the human tuberculosis test results are compared to results using ELISA—negative and positive results are shown whereby it may be seen that the present test process and ELISA provide similar results. Also, the human tuberculosis test results were compared where a readout of impedance Z change percent over time was taken versus a read-out of capacitance C over time with equivalent results. In other words, impedance over time may be equivalently measured over time to capacitance.

Figure 7A:
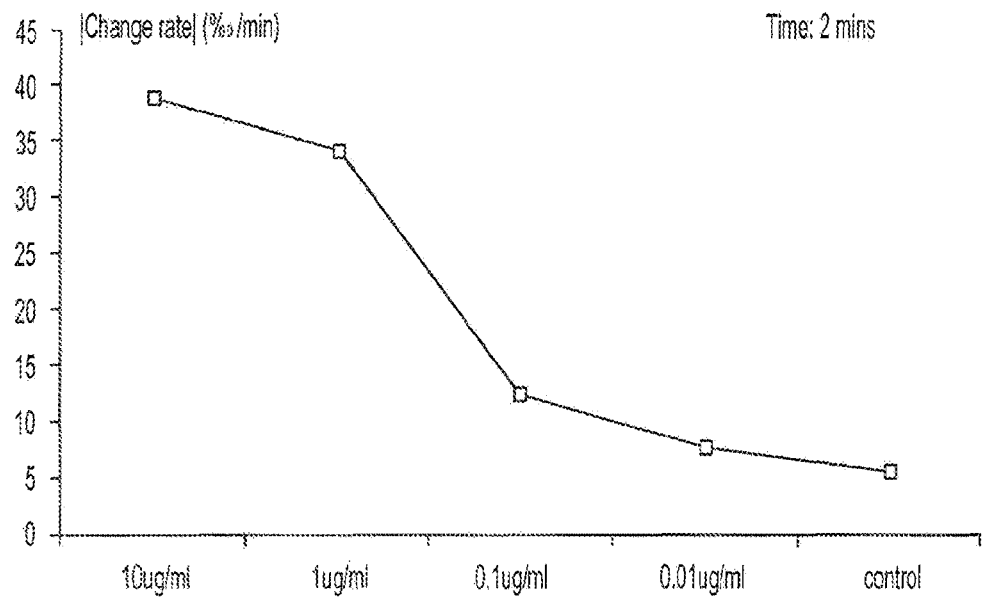
FIG. 7A is a limit of detection graph results for 100 mVrms at 100 kHz and a duration of two minutes versus the change rate in % per minute for control versus various concentrations of micrograms per milliliter.

Referring to FIG. 7A, there is shown limit of detection graph results for a 100 mVrms signal applied at 100 kHz and a predetermined period duration of two minutes in this tuberculosis application versus the change rate in % per minute for control versus various concentrations of micrograms per milliliter, the object being to determine the limits of serum concentration. As can be seen, antibody at concentrations of a range from 1 to 10 µg/mL result in clear differentiation compared with a control. A concentration at 0.1 µg/mL might be considered by some to be acceptable.

Now bovine tuberculosis test results will be discussed where ten negative and ten positive (total of twenty) badger tuberculosis samples were tested and capacitance rate of change over time measured.

A table is provided below showing the results:

TABLE 1

| Sample No. | dC/dt | Conclusions from Capacitance Measurement | Results of ELISA |
|---|---|---|---|
| N1 | −31.2174 | P | N |
| N2 | −1.2917 | N | N |
| N3 | 4.6227 | N | N |
| N4 | −18.1005 | P | N |
| N5 | −4.6286 | N | N |
| N6 | −16.4941 | P | N |
| N7 | −4.9776 | N | N |
| N8 | −3.3192 | N | N |
| N9 | −3.2161 | N | N |
| N10 |  | N | N |
| P1 | −21.6996 | P | P |
| P2 | −18.8937 | P | P |
| P3 | −24.9467 | P | P |
| P4 | −12.544 | P | P |
| P5 | −15.9398 | P | P |
| P6 | −19.0317 | P | P |
| P7 | −26.0158 | P | P |
| P8 | −38.8778 | P | P |
| P9 | −25.838 | P | P |
| P10 | −19.0333 | P | P |
| Buffer control | .8837 | N/A | N/A |

From the above table, it may be seen that three samples tested positive that should have tested negative out of twenty samples total in comparison with ELISA results. Nevertheless, the bovine tuberculosis tests for the badger samples demonstrated 85% accuracy. It is believed that the improved electrode array of FIG. 9 would provide improved results.

Figure 7B:
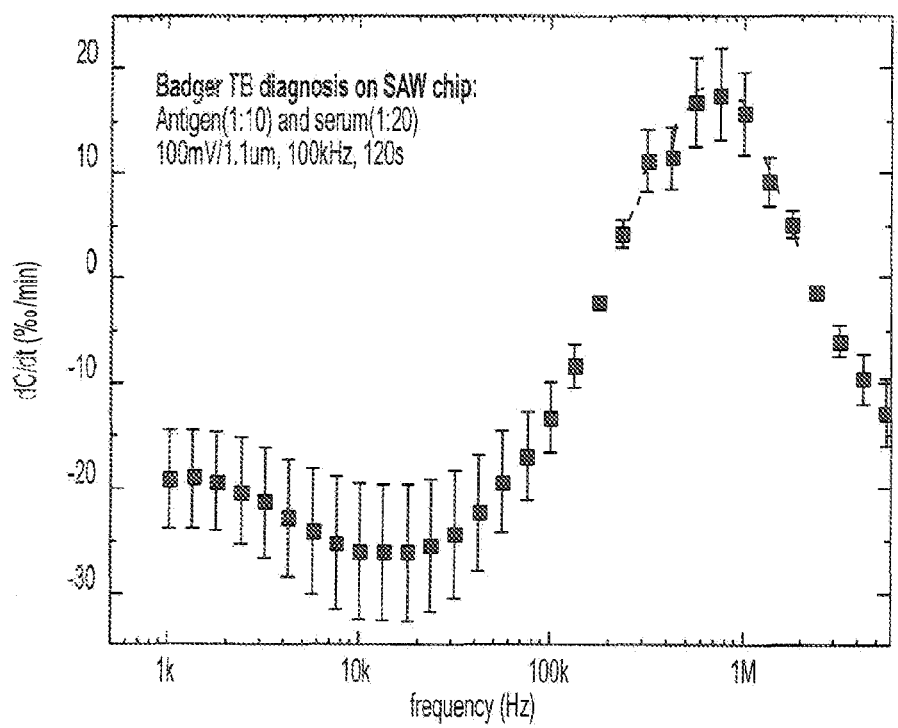
FIG. 7B is a graph showing badger tuberculosis detection by change in capacitance over time versus frequency of applied signal.

Referring now to FIG. 7B, there is shown a graph for badger tuberculosis diagnosis on the SAW resonator electrode array of FIG. 1 with an antigen 1:10 concentration and a serum 1:20 concentration for a 100 mV per 1.1 µm voltage drop signal applied for 120 seconds and frequency varying from 1 kHz to 5 MHz. From an analysis of the graph, one may conclude that 10 kHz to 30 kHz is a preferred frequency range to read the change in capacitance over time data. Similar testing was performed for detection of Johne's disease and will now be discussed with reference to FIG. 8.

Figure 8A:
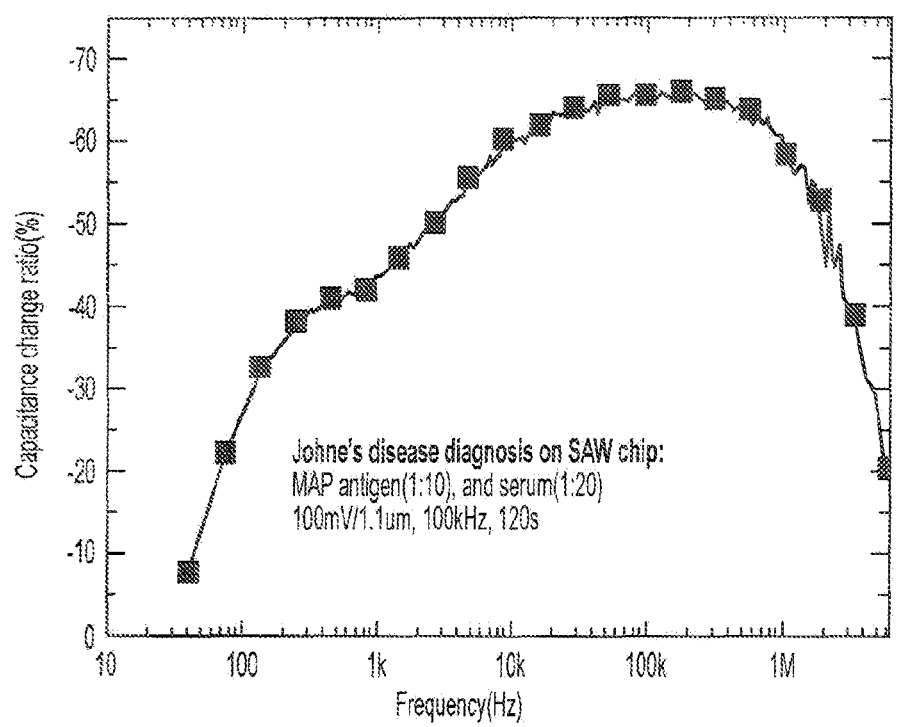
FIG. 8A and FIG. 8B are graphical results of a study of frequency range of applied signal for the circuit of FIG. 1, representing change in capacitance over time versus frequency for Johne's disease diagnosis using the circuit of FIG. 1.
Figure 8B:
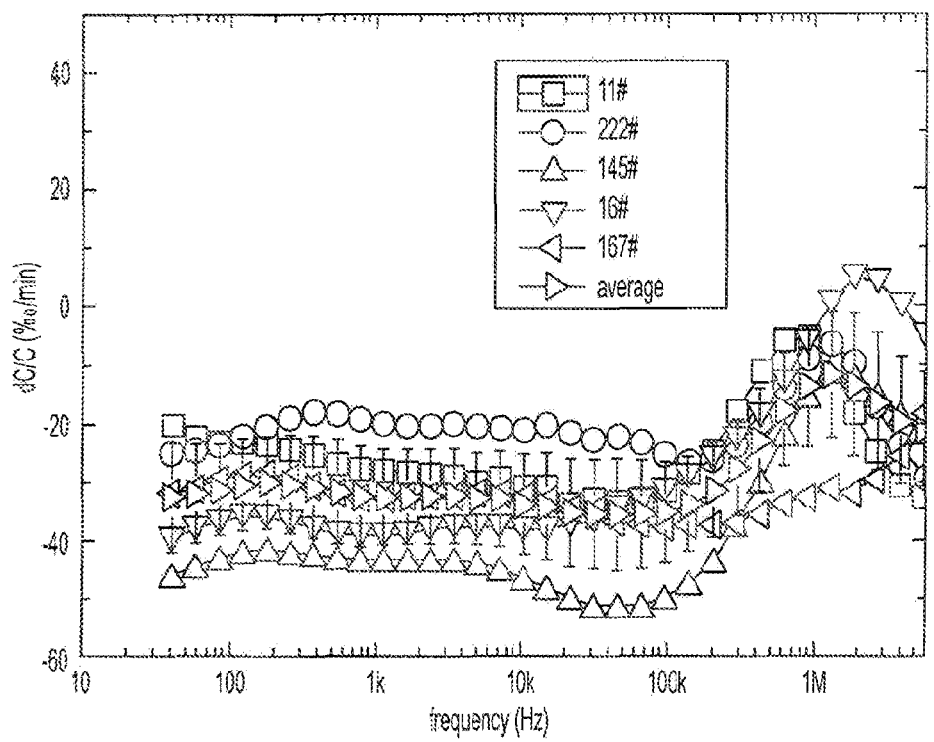
Figure 8C:
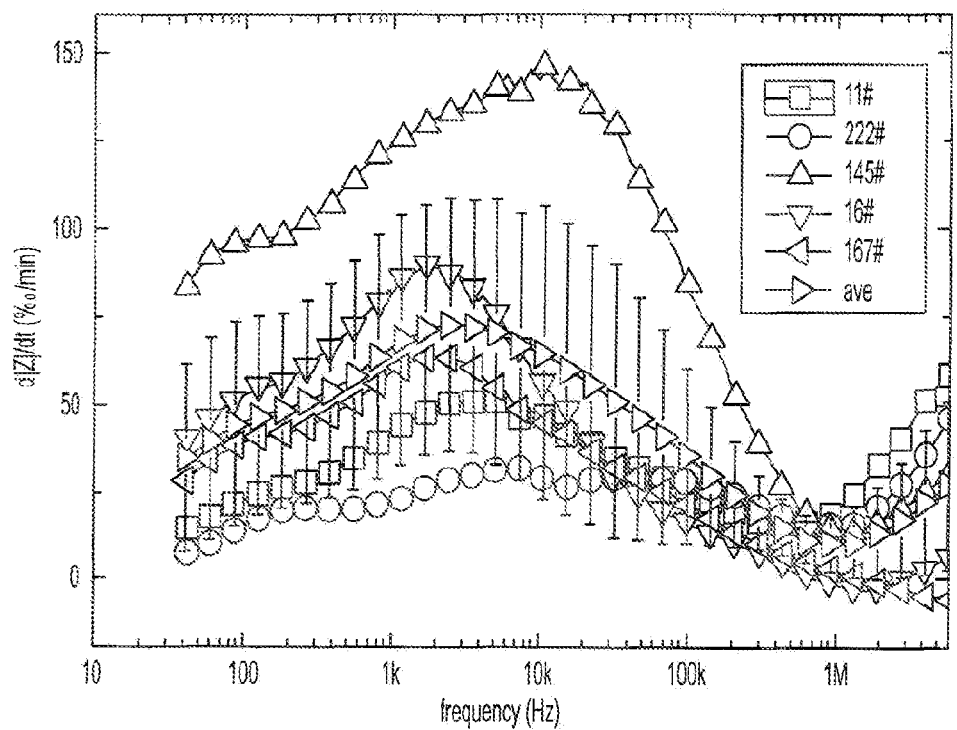
FIG. 8C is a similar graph to FIG. 8B for change in impedance over time versus frequency of applied signal.

Referring first to FIG. 8A, there is shown a graph of Johne's disease diagnosis on the SAW resonator electrode array of FIG. 1 with a M. paratuberculosis (MAP) antigen 1:10 concentration and a serum 1:20 concentration with an applied voltage of 100 mV per 1.1 µmeter over a predetermined duration in this application of 120 seconds or two minutes. From an analysis of the graph, one may conclude that approximately 10 kHz to 100 kHz is a sensitive frequency range to read the change in capacitance over time data. In FIGS. 8B and 8C, the applied signal and concentrations were not changed but FIGS. 8B and 8C represent a graph for five biomarker samples and their average for change in capacitance data over time versus frequency of applied signal while FIG. 8C provides similar results for a change in impedance data over time versus frequency. Tests were conducted from approximately 40 Hz out to 6 MHz in FIGS. 8B and 8C. From FIG. 8B, one may conclude that 1 kHz to 10 kHz is a sensitive frequency range to read capacitance while from FIG. 8C, one may conclude that 1 kHz to 50 kHz is a sensitive frequency range to read impedance change data over time. Consequently, to read either capacitance or impedance data, from FIGS. 8B and 8C, one may conclude that an applied signal be in the range of 1 kHz to 50 kHz.

Figure 8D:
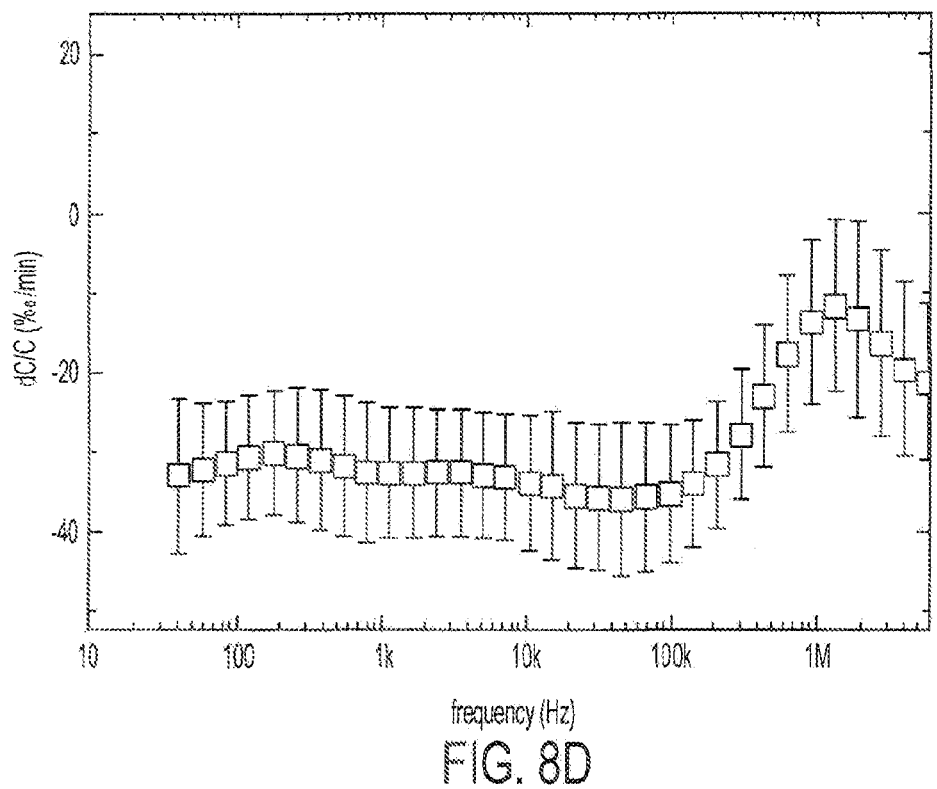
FIG. 8D and FIG. 8E are graphs of change in capacitance and impedance, respectively, over time versus frequency for the circuit of FIG. 1.
Figure 8E:
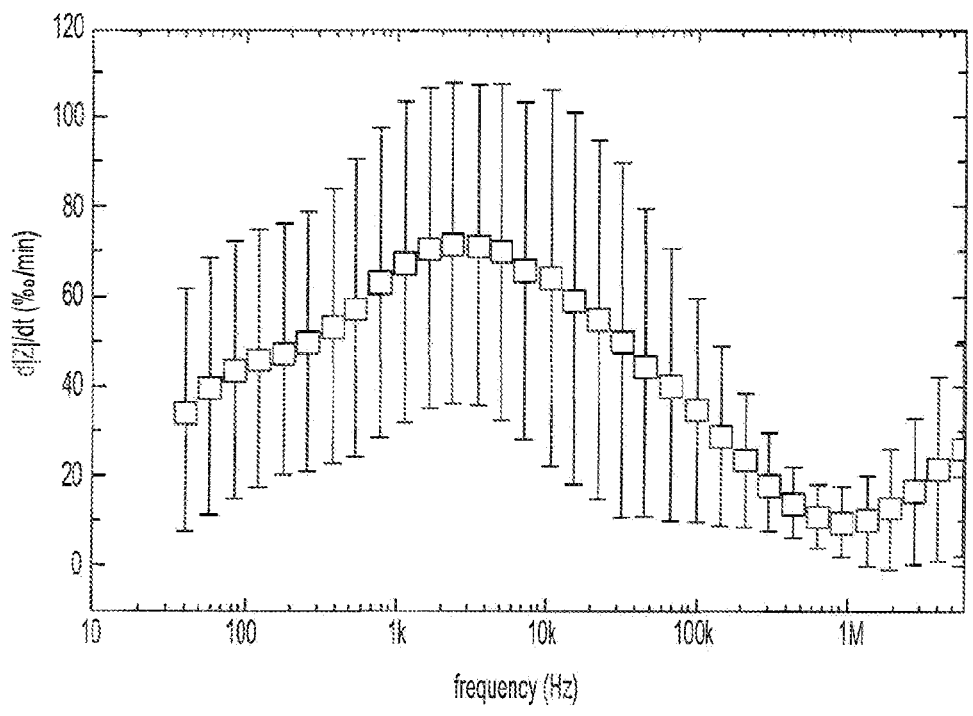

FIGS. 8D and 8E also represent graphs of change in capacitance over time and change in impedance over time data versus frequency of applied signal for detection of Johne's disease using the circuit of FIG. 1 and the same antigen and serum concentrations. The frequency range tested is again from about 40 Hz to 6 MHz. An analysis of FIG. 8D suggests that 10 to 100 kHz is a sensitive frequency range for applied signal to read capacitance data while FIG. 8E suggests that a lower frequency range of 1 kHz to 10 kHz is a sensitive frequency range for applied signal to read impedance data.

The results discussed above for bovine tuberculosis and Johne's disease and for bovine tuberculosis employed ethanol extracts of *Mycobacterium bovis* and *M paratuberculosis* using methods described in U.S. Pat. No. 7,422,869 issued Sep. 9, 2008 and U.S. Pat. No. 7,713,715 issued May 11, 2010 to inventor S. Eda and to C. A. Speer of the University of Tennessee.

Alternative Electrode Array with Improved Performance

Figure 9A:
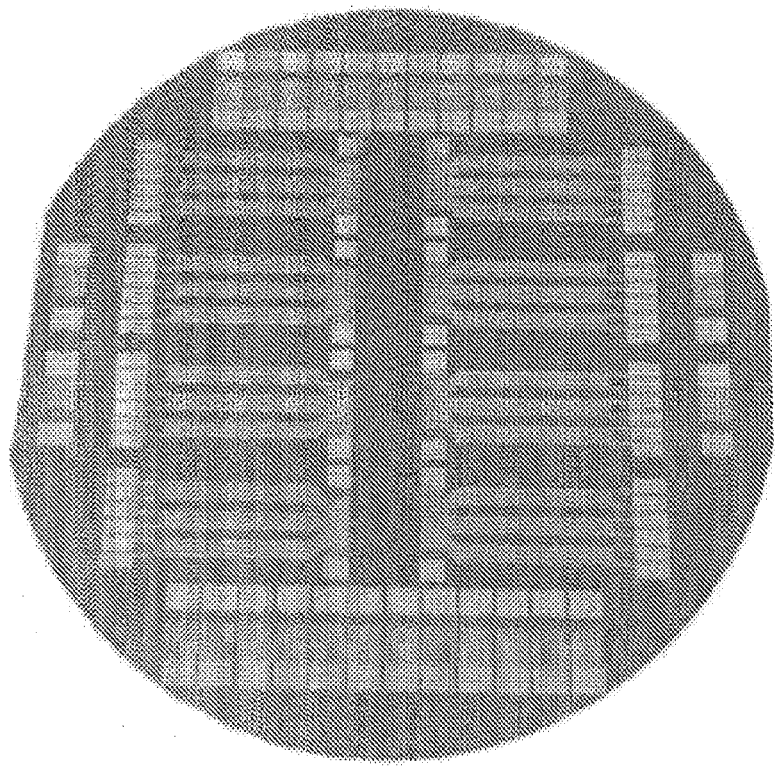
FIG. 9A provides a micrograph view of an electrode array constructed on a substrate which provides improved results over the conventional electrode array of FIG. 1.
Figure 9B:
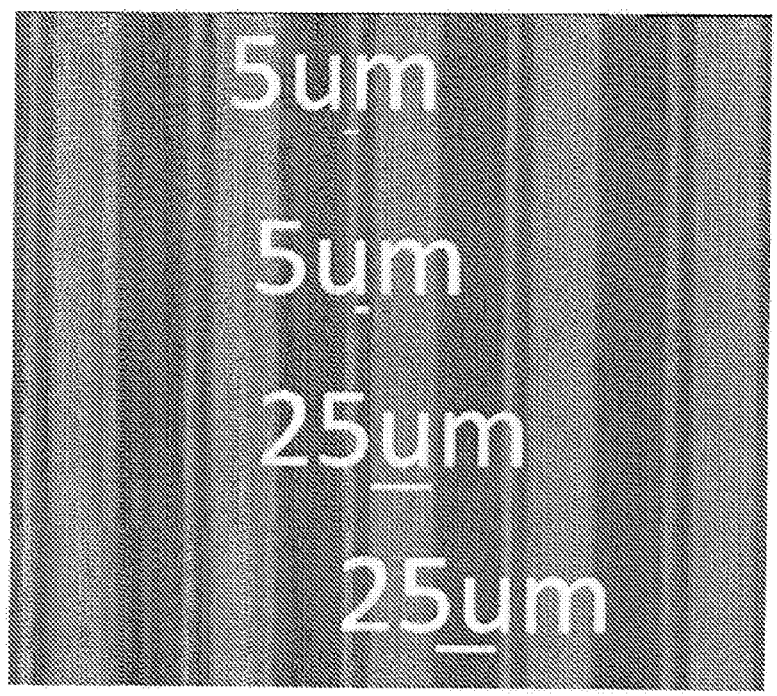
FIG. 9B provides a micrograph showing and interspersed 25, 5, 5, 25 micron pattern that is repeated in the electrode array depicted in FIG. 9A.

FIG. 9A provides a micrograph view of an electrode array constructed on a substrate which provides improved results over the conventional electrode array of FIG. 1. A substrate may be as large as ten centimeters in diameter and comprise twenty electrode arrays for receiving biological test samples. As briefly described above, the electrode array of FIG. 9A provides a substrate of silicon and is constructed using well known photo-lithography processes to provide a repeatable pattern of fingers and spaces between the fingers and as many sample receiving locations as desired keeping in mind a one or two milliliter sample deposit (even microliter deposit depending on concentration level). FIG. 9B provides a micrograph showing an interspersed 5, 5, 25, 25 micron pattern that is repeated in the electrode array depicted in FIG. 8A. A first electrode is shown having a width of 25.1876 µm. A space is then provided of width 5.140960 µm. The next conductor has a width of 5.497225 µm. The final separation before the pattern repeats is 25.09273 µm. Note from FIG. 9A that a plurality of electrode arrays may be distributed on the surface of the same chip for receiving and testing multiple samples simultaneously. Other electrode configurations may include pin-line coplanar electrodes and face-to-face patterned electrodes. Microelectrode designs that produce non-uniform electric fields may be implemented as a laboratory on a chip. An electrode mesh formed as a capacitor will be discussed with reference to FIGS. 19A-19D and a further electrode array will be discussed with reference to FIG. 23.

FIG. 10 provides a drawing similar to FIG. 3B showing how the electrode array may provide improved binding results between an antigen/antibody against pathogen coating layer, invoking long range AC electrokinetic microflows. The electrode array may comprise a substrate of silicon Si 905. The 5, 5, 25, 25, 5, 5, 25, 25 finger/space pattern are repeated across the substrate whereby +V cos ωt, −V cos ωt, +V cos ωt and −V cos ωt are generated by the applied electrical signal of given magnitude and frequency. An antigen/antibody against pathogen coating layer 920 is shown above with the antigen/antibody against pathogen appearing as Y shaped-receptors for binding or not binding molecules by AC electrokinetics. Molecules of the antigen/antibody against pathogen coating layer are shown moving toward the five micron spaces between the five micron fingers and the 25 micron fingers and move away from the 25 micron spaces and then back again. From the design of FIG. 9 and in comparison with the design of FIG. 1, it may be concluded that a range in finger values may be successful in testing for bacterial diseases between one and perhaps 100 microns. Similarly, the range in spacing between fingers may be between a range of from one and perhaps 100 microns with successful test results. While gold/chromium was used for the composition of the electrodes, other conductive metals may be used to advantage such as gold/titanium, gold, silver, aluminum and copper. Also discussed subsequently herein is the effectiveness of the application of a coating versus no coating of the electrodes.

In practice, twenty Johne's disease tests were performed—ten negative and ten positive as before with the electrode array of FIG. 1 with the following results. For testing negative, the range was between −2.6356 and +0.7537% change. For testing negative, the range was between −52.3152 and -83.8032% change. These ranges demonstrate a greatly improved differentiation between capacitive change rates between the micro-fabricated 5-5-25-25 chip and the commercially available electrode array for Johne's disease. The applied signal in these tests was at 500 mV and 100 kHz.

Figure 11:
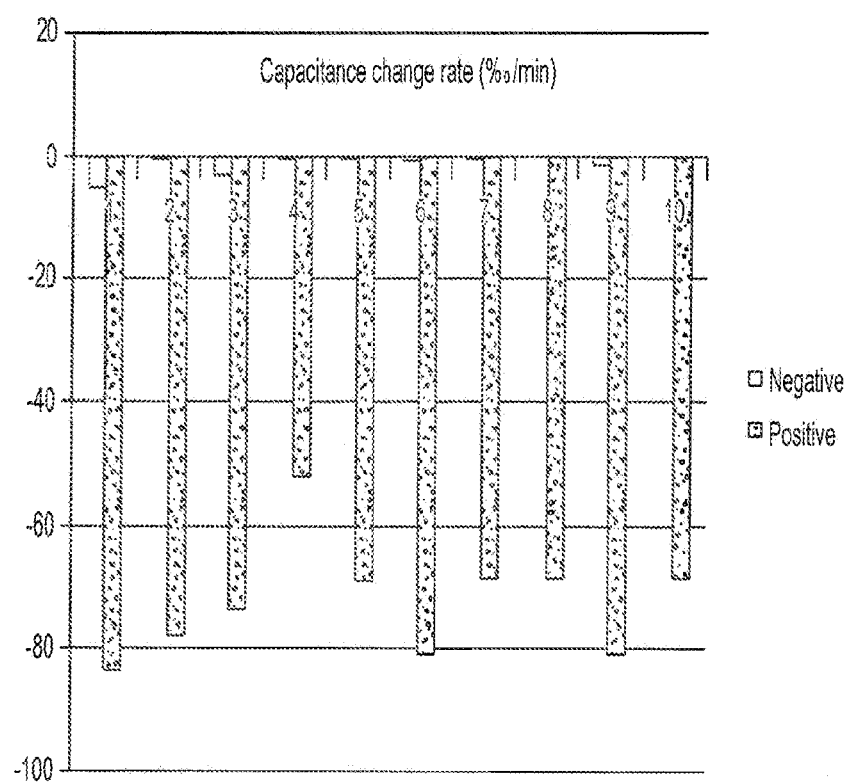
FIG. 11 provides a graphical example of improved negative/positive differentiation between capacitance rate of change in % per minute for ten negative and ten positive samples.

FIG. 11 provides a graphical example of the improved negative/positive differentiation between capacitance rate of change in % per minute for ten negative and ten positive samples of Johne's disease showing the dramatic differentiation between results.

Figure 12:
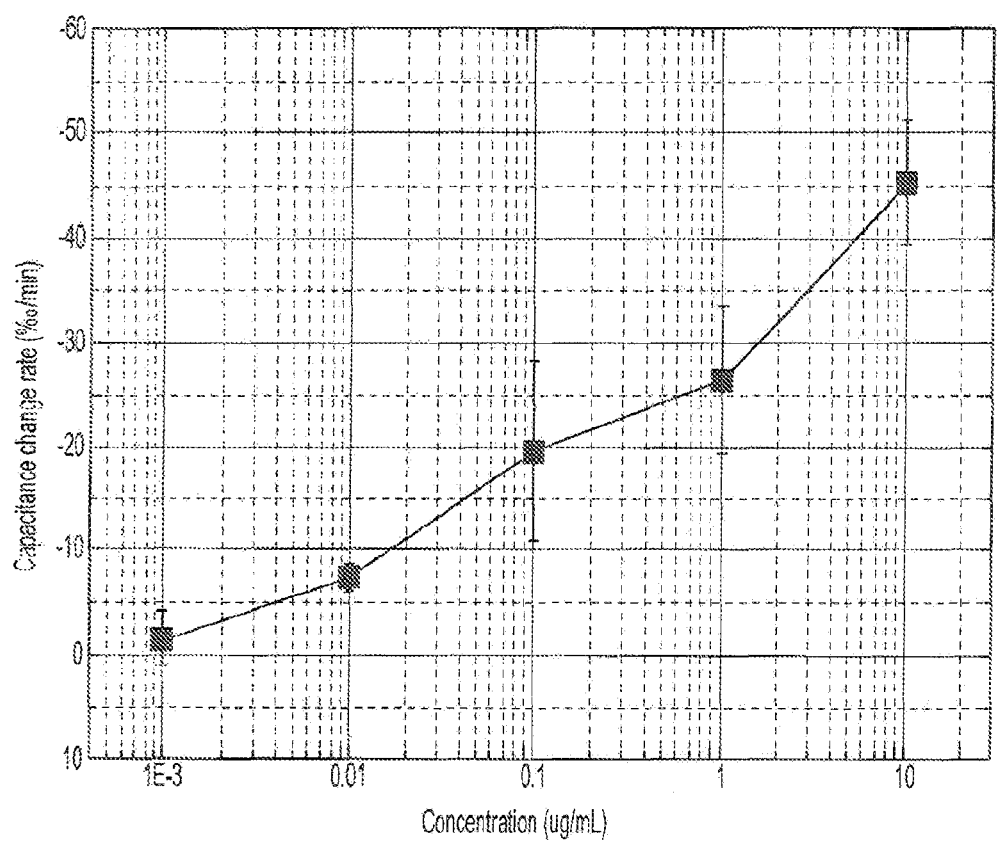
FIG. 12 provides a graph of capacitance change rate in % per minute versus concentration in micrograms per milliliter.

FIG. 12 provides a graph of capacitance change rate in % per minute versus concentration in micrograms per milliliter to show the limits of detection using the chip of FIG. 9. As seen in the graph, concentrations as low as 0.01 µg per mL demonstrated acceptable results at 500 mV signal and 100 kHz signal frequency.

Figure 13:
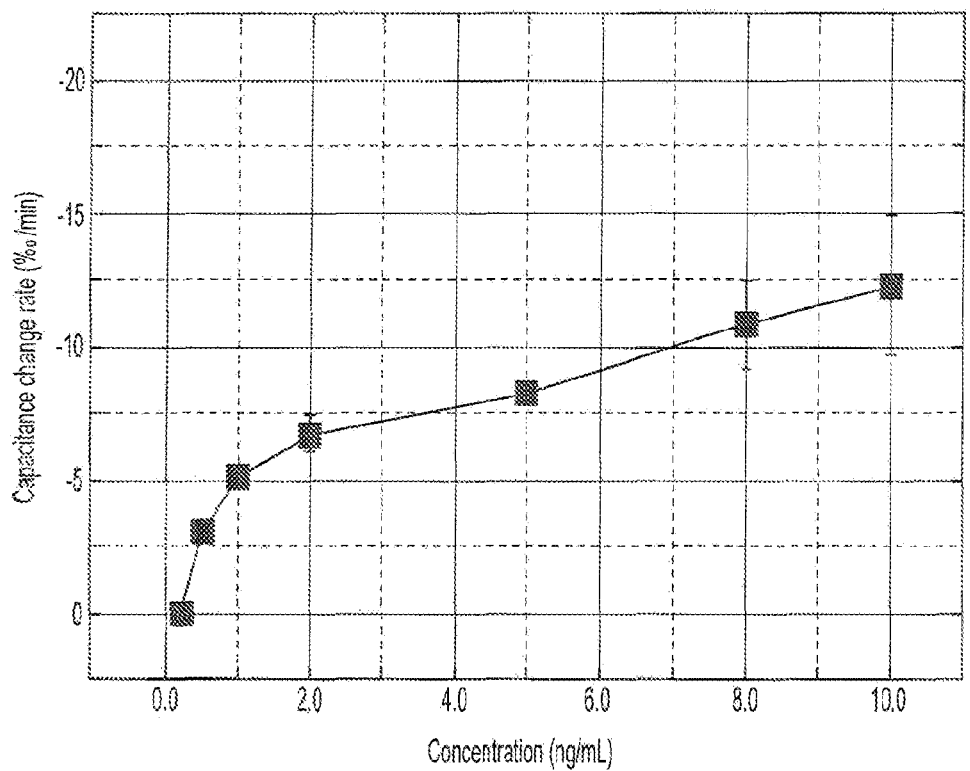
FIG. 13 provides a graph of capacitance change in % per minute versus concentration in nanograms per milliliter.

FIG. 13 provides a graph of capacitance change in % per minute versus concentration in nanograms per milliliter. The signal strength is raised to 1 Vrms and an acceptable level of detection is seen from the graph at 0.5 ng/mL concentration.

Figure 14:
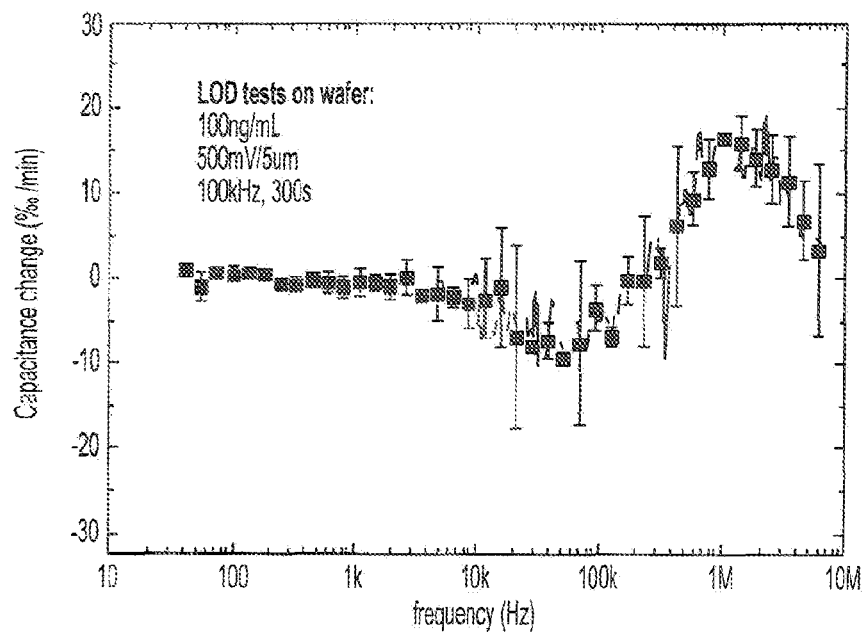
FIG. 14 provides a graphical representation of limit of detection testing for the wafer array of FIG. 9 showing capacitance change over time versus frequency of applied signal.

FIG. 14 provides a further limit of detection test on the wafer of FIG. 9 for a concentration of 100 nanograms per milliliter and an applied signal at 500 mV per five microns of electrode finger where capacitance change over time is graphed versus frequency of applied signal from 10 kHz to 10 MHz. The tests were conducted over three hundred seconds (five minutes) over a frequency range from about 40 Hz to about 6 MHz. From an analysis of the graph of FIG. 14, one may conclude that a frequency range of from 10 to 100 kHz is a sensitive frequency range for reading the capacitance change over time data for the wafer of FIG. 9 which compares favorably with the sensitive frequency range for the SAW electrode array of FIG. 1.

Example 3A—Pathogen Detection (Mastitis)

Referring now to FIGS. 15 through 19, pathogen detection for mastitis will be discussed wherein milk samples may be taken from lactating animals. *Streptococcus uberis* is a species of *Streptococcus*. Protein G is an immunoglobulin-binding protein expressed in group C and G Streptococcal bacteria much like Protein A but with differing specificities. It is a 65-kDa (G148 protein G) and a 58 kDa (C40 protein G) cell surface protein that has found application in purifying antibodies through its binding to the Fc region. Protein G is used for preparation of each of the experimental group and control group specimens used in blocking of the lab-on-a-chip and bacteria shown in FIG. 15.

Figures 15, 16A:
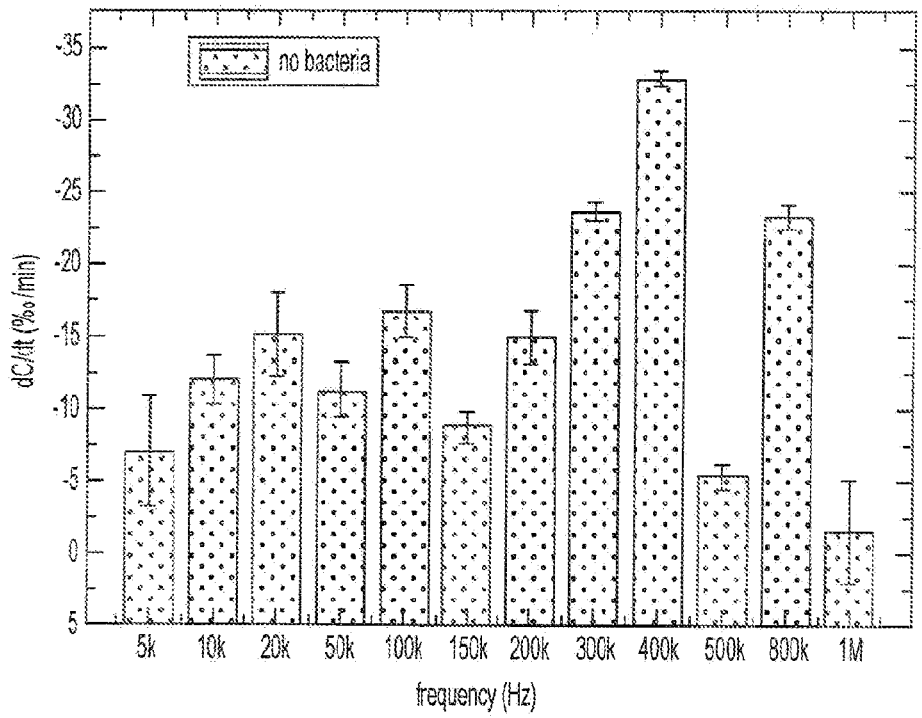
FIG. 15 provides a table for pathogen detection involving two control groups and one experimental group where the experimental group includes *Streptococcus uberis* (causative agent of mastitis) bacteria and describes a process whereby an applied signal frequency range at 100 mV and a brief time period for testing are analyzed.
FIGS. 16A, 16B, and 16C respectively provide graphs of a negative control group that omitted bacteria (labeled "no bacteria"), a negative control group that eliminated serum (labeled "no serum"), and an experimental group with serum and bacteria (labeled "bind"). Each bar of the respective graphs represents percent change in capacitance over time versus frequency of applied signal between five kHz and one MHz.

Referring to FIG. 15, two negative control groups and one experimental group were involved in pathogen detection. Protein G, per FIG. 15, may be incubated at a concentration of ten micrograms per milliliter and an amount of two milliliters in a humidor overnight to use in coating an electrode array as described above. In the area identified Block, control (no serum), Buffer B is shown at 0.1× concentration in an amount of two microliters for one hour. The experimental blocking solution may contain serum diluted 1:10 in Buffer B. The array was washed with PBST at 0.1× concentration using two microliters twice. The Bacteria portion of FIG. 15 comprises *S. uberis* bacteria at $1\times10^7$ cell count (the same cell density per milliliter of bacteria that is reached in milk bacterial counts) using two microliters in 0.1×PBS solution as the experimental group. The control, no bacteria, may be PBS at 0.1× concentration and two microliters.

Three frequency sweeps were conducted for pathogen detection per FIG. 15. Sweep 1 was at a signal magnitude of 5 mV between 40 Hz and 6 MHz for one second. Sweep 2 was at a signal magnitude of 100 mV and the sweeping frequency taking 201 measurement points was at 5 kHz, 10 kHz, 20 kHz, 50 kHz, 100 kHz, 300 kHz, 500 kHz, 800 kHz, and 1 MHz. A third frequency sweep (Sweep 3) was between 40 Hertz and 6 MHz for one second (similar to Sweep 1) at 5 mVrms. Sweep 2 was the experimental sweep to test for appropriate frequency and maintain a change in capacitance over time demonstrating diagnosis of bacterial disease (mastitis) versus control change in capacitance by comparing bacterial solution binding of the pathogen detection coating at different frequencies to control groups. These results are demonstrated in FIG. 16.

Referring now to FIG. 16A, there is shown a graph of percent change in capacitance over time for control group serum of 0.1× concentration PBS with no bacteria, Sweep 2 results only. The negative control group with no bacteria demonstrates a maximum percent change in capacitance over time when the signal is at 400 kHz. At 800 kHz and at 300 kHz the percent change in capacitance over time is slightly reduced. At 50 kHz, the percent change in capacitance over time is decreased more still.

Figure 16B:
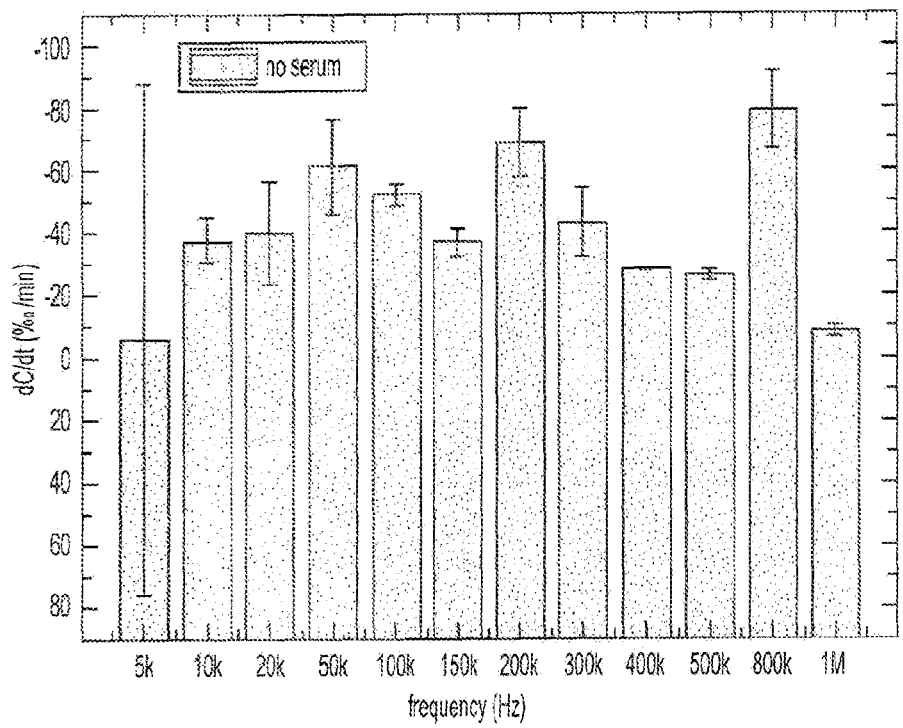

Referring now to FIG. 16B, there is shown a graph of percent change in capacitance over time for negative control group solution with no specific serum antibody, Sweep 2 results only. The negative control group demonstrates a maximum percent change in capacitance over time when the signal is at 800 kHz. At all other frequencies in the sweep, the percent change in capacitance was significantly less (better).

Figure 16C:
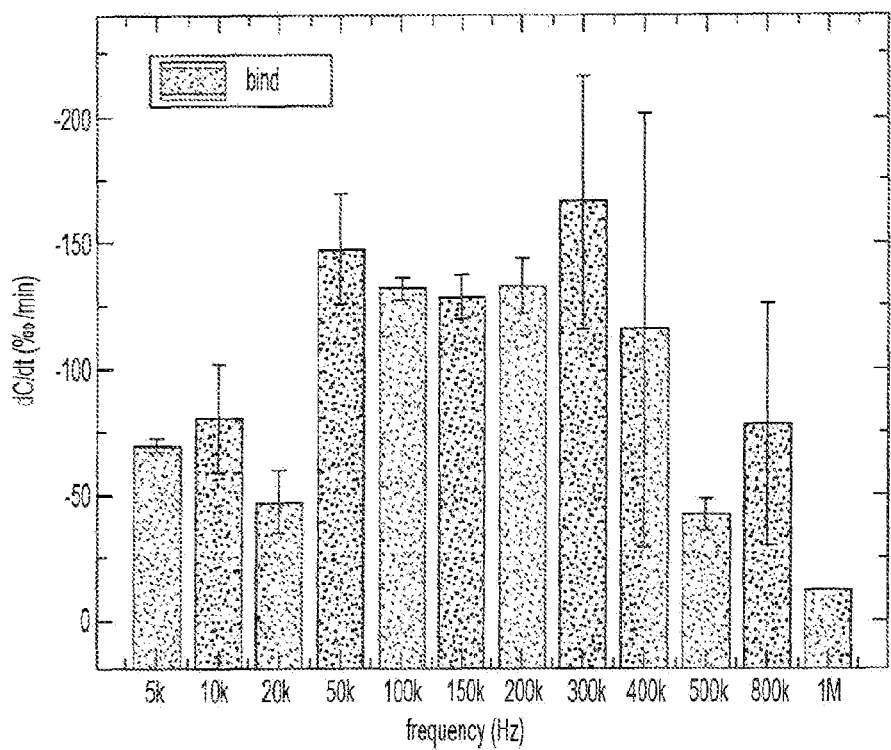

Referring now to FIG. 16C, there is shown a graph of percent change in capacitance over time for the bacterial solution (S. uberis/mastitis) binding to the antibody serum, Sweep 2 results only. The bacterial solution group demonstrates a maximum percent change in capacitance over time when the signal is at 300 kHz and again at 50 kHz. At 100 and at 200 kHz, the percent change in capacitance was lower.

Figures 16D, 16E:
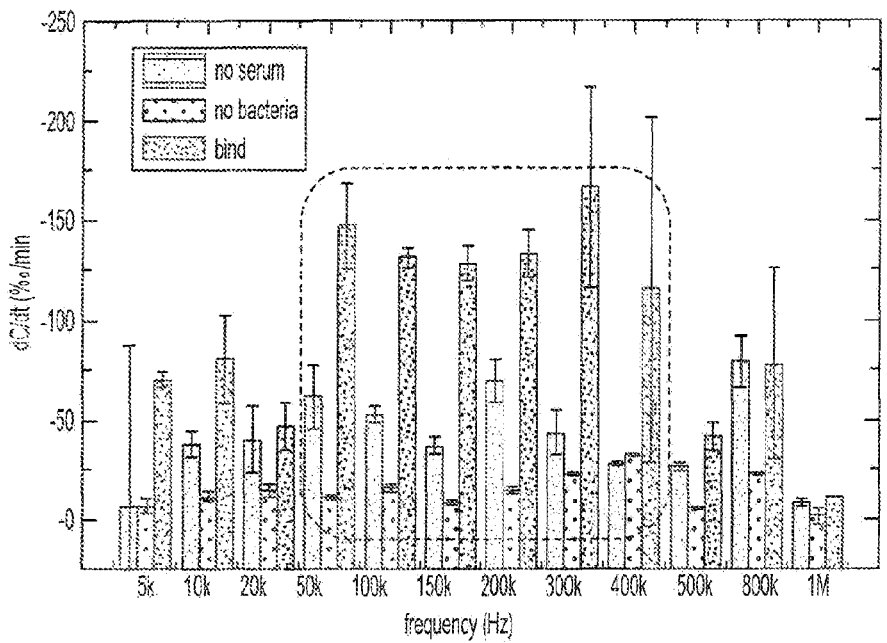
FIG. 16D provides a combined graph showing results of FIGS. 16A, 16B and 16C, wherein 300 kHz appears appropriate for use in detecting *Streptococcus uberis* bacteria.
FIG. 16E provides a data table for each measured frequency, percent change in capacitance and standard deviation for each of no bacteria, no serum and bind.

The results are summarized in FIG. 16D, which is a combined graph showing the results of FIGS. 16A, B and C superimposed on one another where the gray scale shows that for each frequency, the percent change in capacitance over time is shown in the order of no serum, no bacteria and bind from left to right. At all frequency points in FIG. 16D, binding exceeds serum and bacteria control except the frequency results for 800 kHz. One may conclude from the graph that an applied signal between 50 kHz and 4000 kHz at 100 mV for sixty seconds (Sweep 2 signal parameters) appropriately distinguish S. uberis binding from negative controls. FIG. 16E provides a chart of all data taken and calculated standard deviations for all points.

Figure 17:
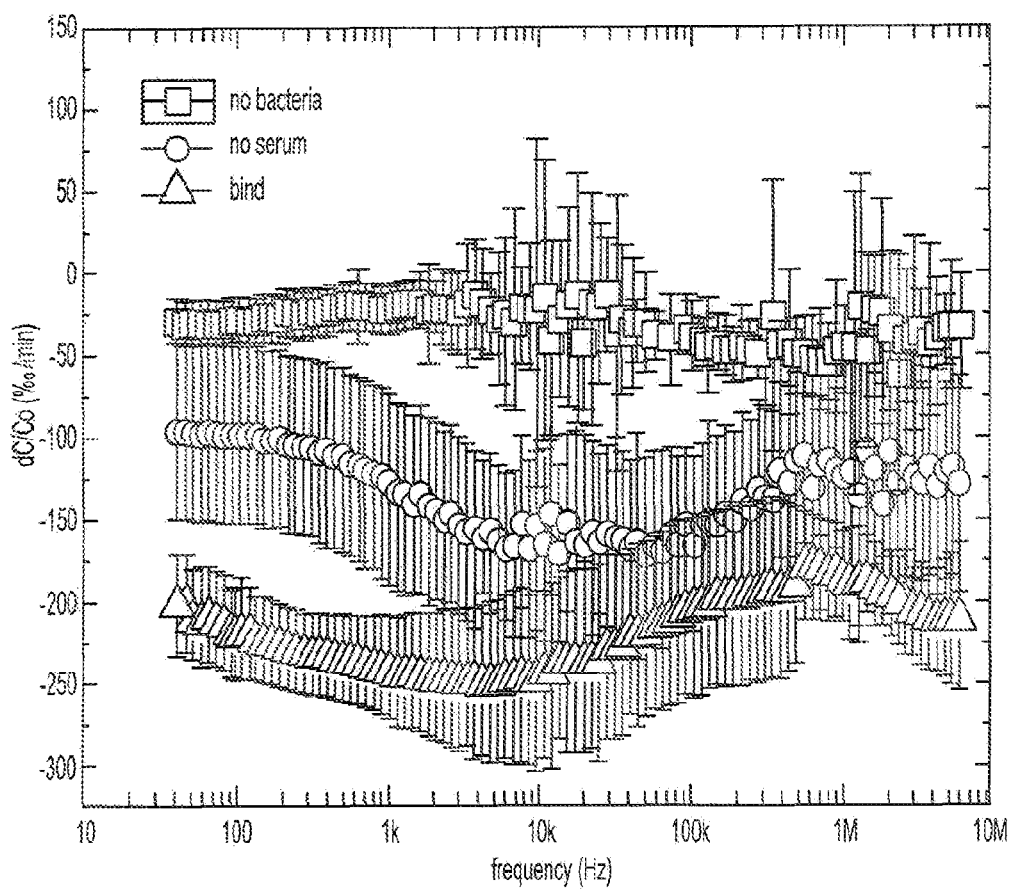
FIG. 17 provides a graph of percent change in capacitance over time for a frequency plot between 40 Hz and 6 MHz whereby a conclusion may be reached that 40 Hz to 1 kHz is a sensitive frequency to read change in capacitance (no overlap in dC/Co percent change values).

Referring now to FIG. 17, there is shown a graph calculated by Sweep 3-Sweep 1 per sixty seconds where the percent change in capacitance over time curves at nine different frequencies show the averaged changes from reactions. From the graph, one may conclude that between 40 Hz and one kHz is a sensitive frequency range to read percent change in capacitance over time by the differentiation of experimental group (binding) versus either negative control groups (no serum or no bacteria) over that range.

Figure 18A:
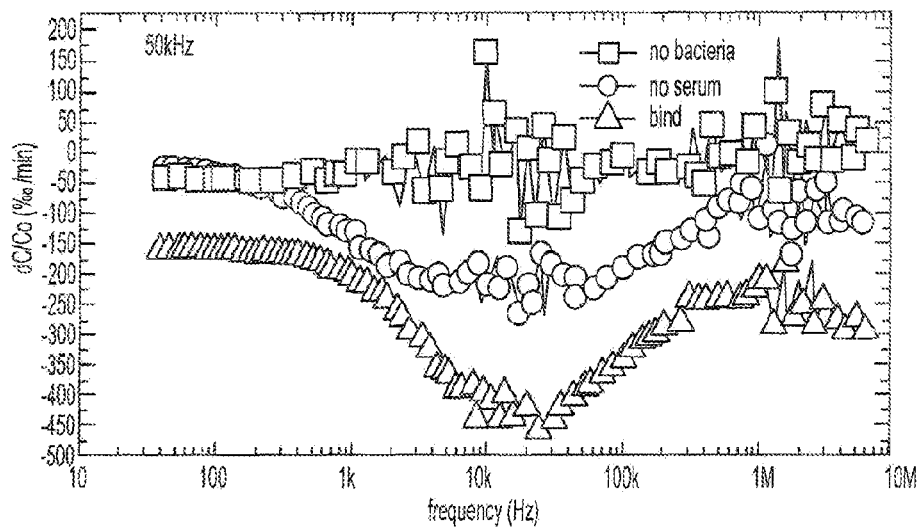
FIGS. 18A, 18B, and 18C are respectively summary graphs for each of 50 kHz, 150 kHz and 300 kHz, a preferred 300 kHz applied signal showing that a sensitive frequency at 300 kHz applied signal for more pronounced differentiation for impedance/capacitance measurement may be between 40 Hz and one kHz as suggested by FIG. 17 for *Streptococcus uberis* bacteria detection (mastitis).
Figure 18B:
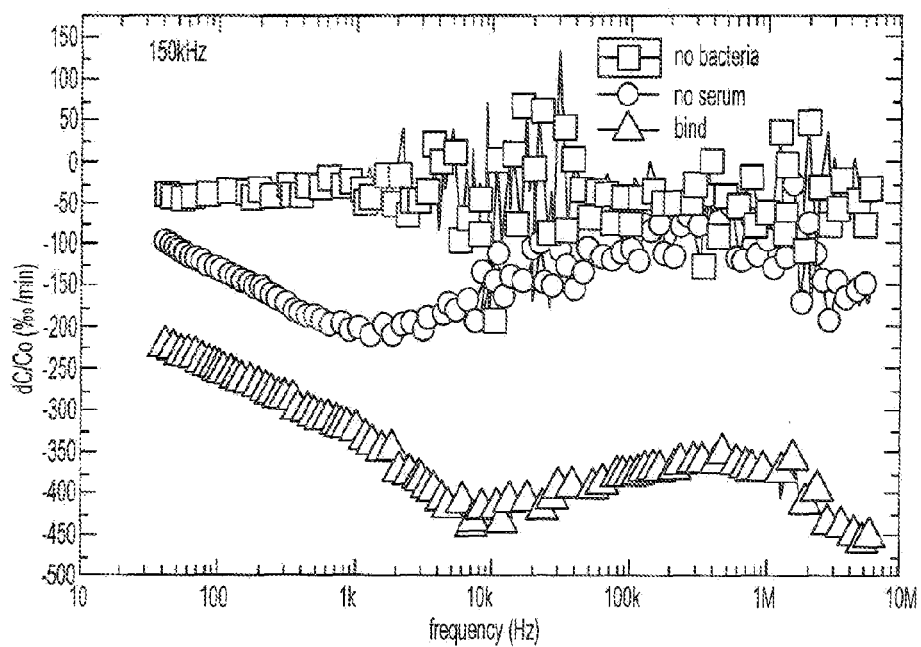
Figure 18C:
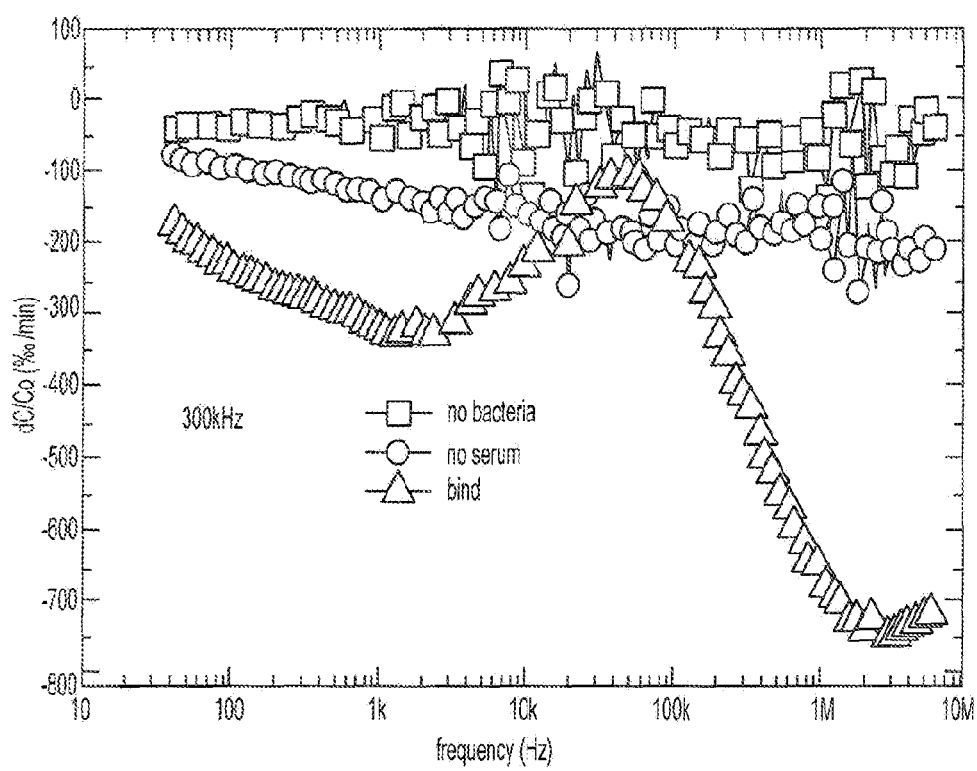

In FIGS. 18A, 18B and 18C, there are shown respective graphs of percent change in capacitance over time calculated by Sweep 3-Sweep 1 per sixty seconds where the percent change in capacitance over time curves were studied for signals at 50 kHz, 150 kHz and 300 kHz, the preferred signal frequencies calculated from FIG. 16D. It may be concluded from this graph that there is more pronounced differentiation when the capacitance or impedance percent change is taken at lower frequencies such as between 40 Hz and two kHz. Note that between these frequencies, experimental group (binding), the lowest curve for 300 kHz (FIG. 18C), provides significantly greater percent change in capacitance than negative control groups no bacteria or no serum at 300 kHz. Above ten kHz, experimental group (binding) and no bacteria and no serum become close together so that binding may not be easily distinguished. Note also that between these frequencies, binding, the next to the lowest curve, at 50 kHz applied frequency, distinguishes from the bacteria curve just above at a range of frequencies, between 100 Hz and one KHz, and the differentiation is not as pronounced but then moves apart again, for example, at 10 kHz. The 150 kHz set of FIG. 18B appears to demonstrate a clear detection of binding across the entire frequency spectrum. In summary, it appears from this graph that differentiation of mastitis/S. uberis is preferred at a 150 kHz or 300 kHz signal frequency and between 40 Hz and ten kHz. The bacteria may be distinguished with a sixty second or one minute test at 100 mV applied signal on an electrode array coated as described.

Example 3B—Somatic Cell Count (Mastitis)

Figure 19A:
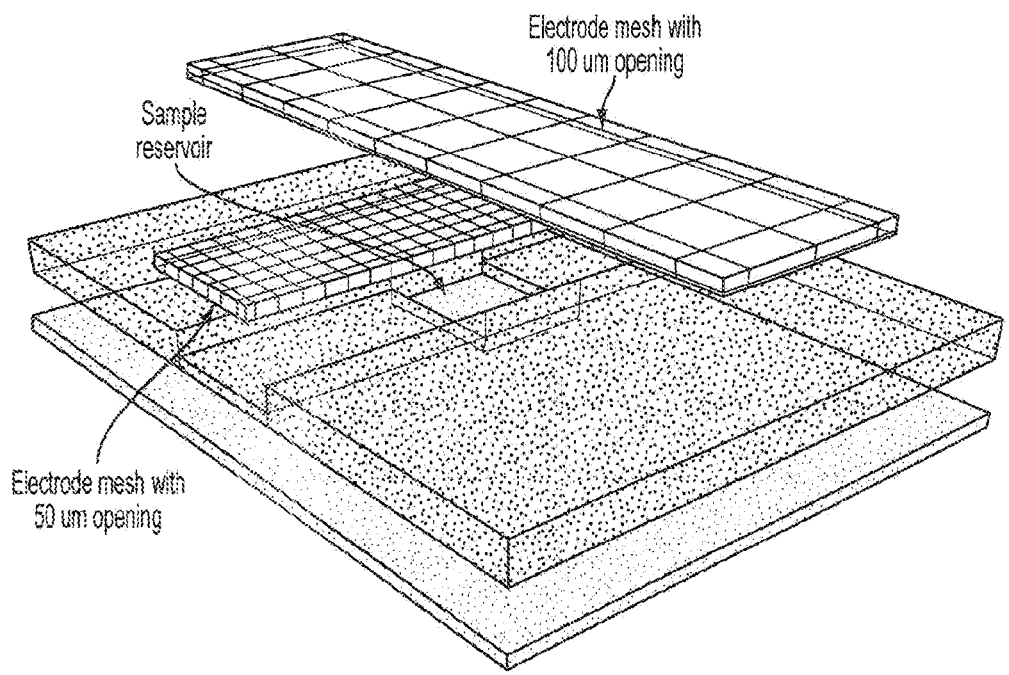
FIG. 19A is a diagrammatic view of a substrate and overlaying electrode meshes of differently sized openings for white blood cell count, for example, for detection of mastitis in cattle.
Figure 19B:
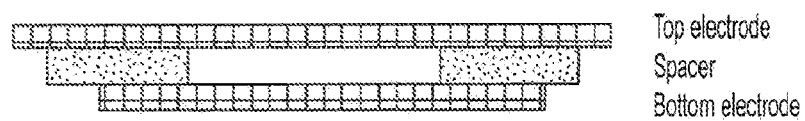
FIG. 19B is a diagram showing a spacing of the top and bottom electrode meshes of FIG. 19A.
Figure 19C:
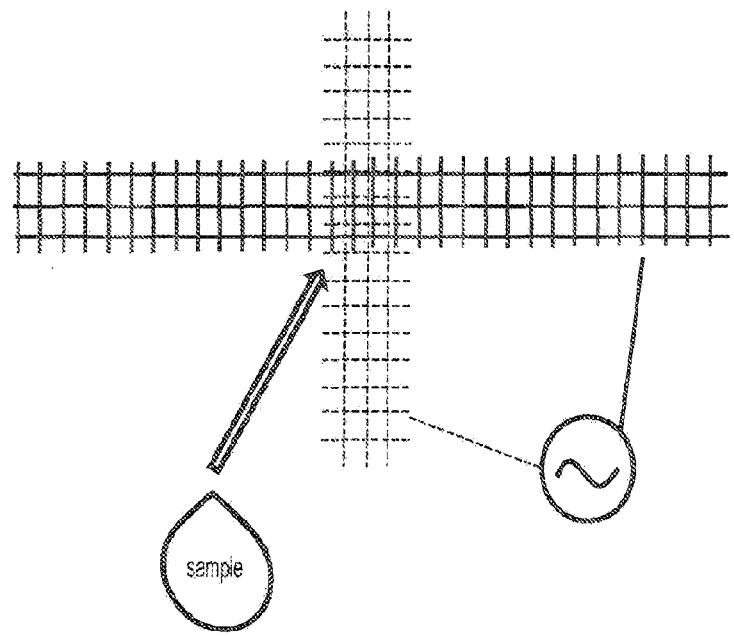
FIG. 19C is a diagram showing how a sample is dropped on the overlaying electrode meshes and a particular alternating current signal applied to the meshes of FIG. 19A.
Figure 19D:
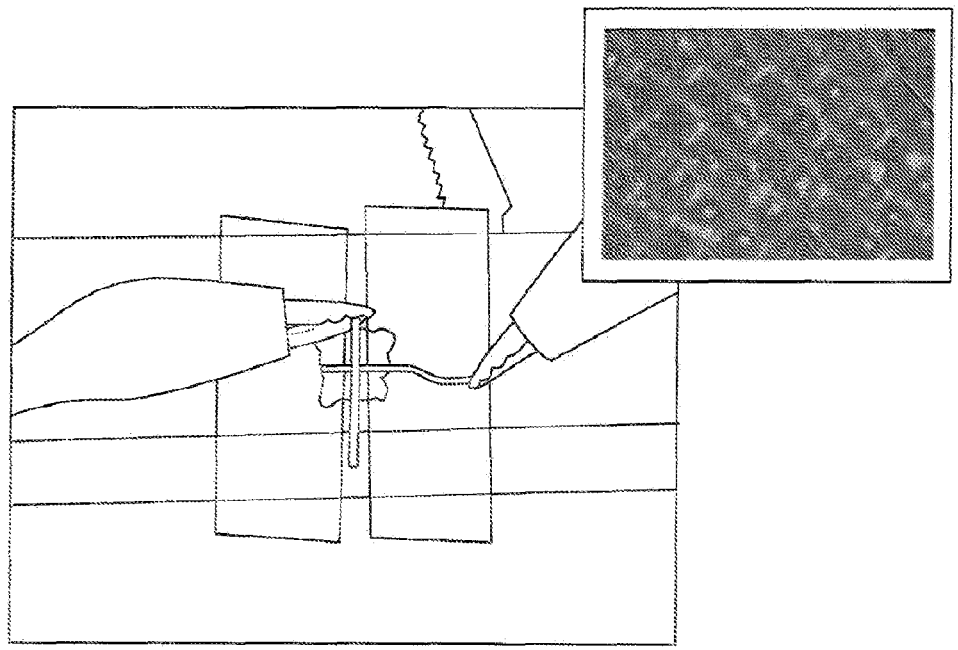
FIG. 19D is a black and white line drawing of a photograph of the overlaying mesh electrodes on the substrate of FIG. 19A.

FIG. 19A provides a view of a substrate and overlaying electrode meshes of differently sized openings for white blood cell count, for example, for detection of mastitis in cattle. The somatic cell count measures the number of somatic cells (immunocytes, like neutrophiles) in milk samples According to FIG. 19A, an electrode array comprising a top electrode mesh with, for example, a one hundred μmeter opening may be overlaid and spaced from a bottom electrode mesh with, for example, a smaller fifty μmeter opening, the object being to permit true biomarker sample to pass through the top and bottom electrode meshes to reach, for example, a sample reservoir or an opening (not shown) to allow the sample to be collected and/or cleaned from the array, such that the embodiment of FIG. 19A promotes an opportunity to detect mastitis via somatic cell count via change in capacitance as described above. In practice, the top electrode may have between a 10 and 500 micron opening (preferably between 50 and 150 micron opening) and the bottom electrode between 5 and 150 micron spacing (preferably between twenty and eighty micron spacing) depending on the lactating animal under test, cattle, goat, sheep and the like. FIG. 19B shows a spacing between the top and bottom electrode meshes (two plates of a capacitor), the two meshes or grid networks forming a capacitor. As used herein and in the claims, a first "mesh" comprises a network-patterned, for example, rectangular network electrode comprising a first electrode array, with or without openings. The mesh underneath may likewise include or not include openings. In other words, a mesh may be solid. The second mesh is shown under the first mesh and provided with a spacing between the meshes to form a capacitor. In an embodiment of FIG. 19A, a sample passes through and reaches a reservoir. In alternative embodiments, a patterned network mesh may be a solid surface with no openings and the sample may rest on the top of two meshes forming a capacitor or pass through a top mesh to a solid bottom mesh. FIG. 19C provides a diagram showing how a sample is dropped on the overlaying electrode meshes and a particular alternating current signal applied to the meshes. FIG. 19D provides a black and white line drawing of a photograph of the overlaying mesh electrodes on the substrate and an expanded view showing the overlaid electrode meshes of one embodiment.

Figure 20A:
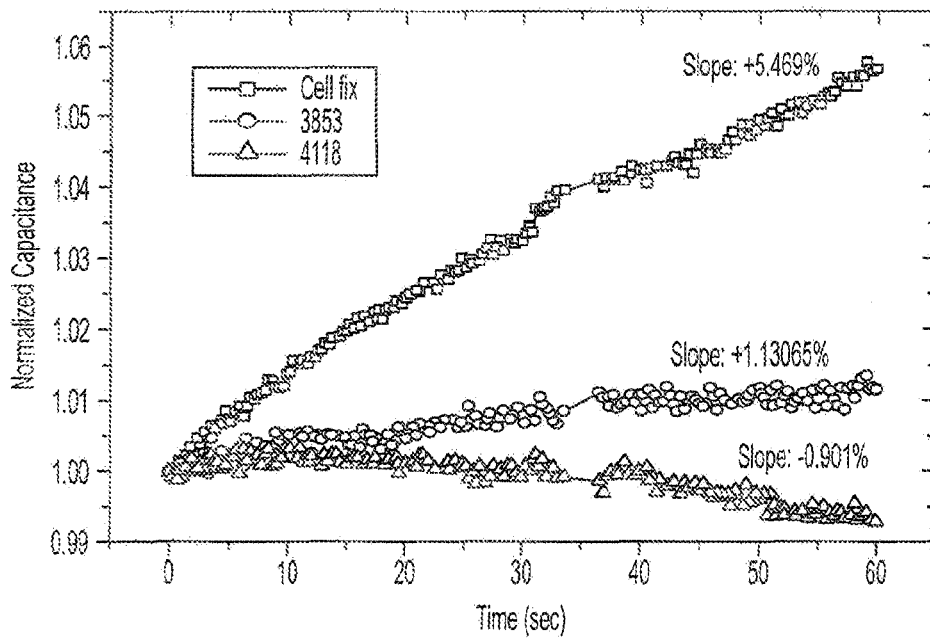
FIGS. 20A, 20B, and 20C respectively provide graphs of resulting normalized capacitance over time (a one minute test) and a demonstration of specificity showing in FIG. 20A curves for cell fix, sample no. 3853 and sample no. 4118.
Figure 20B:
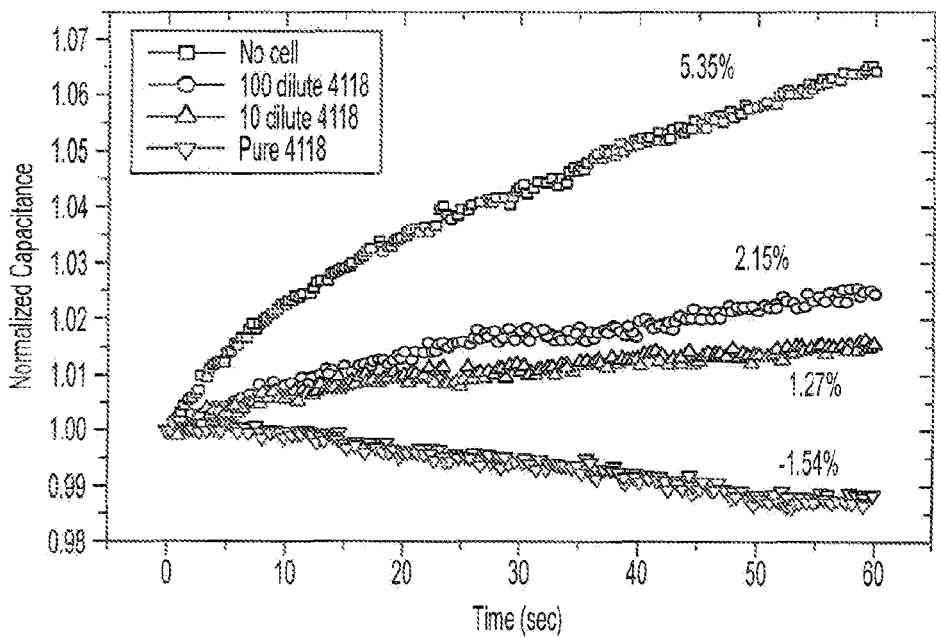
Figure 20C:
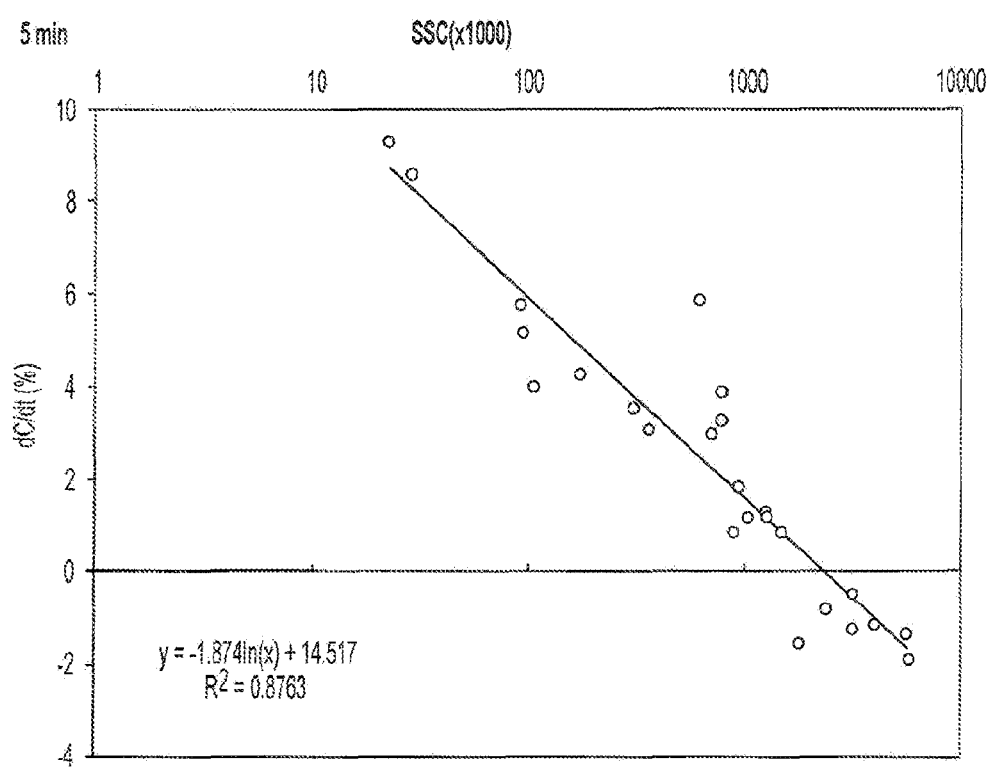

Sample 3853 comprises, for example, a particle density of $1.92 \times 10^6$ particles per milliliter and sample 4118 may comprise a particle density of $3.5 \times 10^6$ particles per milliliter. These samples comprise somatic cell (milk) samples taken from lactating animals. FIG. 20A provides a graph of resulting normalized capacitance over time (a one minute test) showing in FIG. 20A curves for cell fix (no cell), sample no. 3853 and sample no. 4118. The experimental method is exactly the same as was used for devices described above. The capacitance of cell fix (no cell) solution shown in boxes and of sample 3853 increased 5.469% and 1.13065% in a one minute (60 second) test with an applied frequency of 100 kHz and a voltage of 500 mV of applied signal to the overlaid electrode mesh array of FIGS. 19A-19D. FIG. 20B investigates levels of concentration of sample 4118 versus no somatic cells to show that 100 dilute sample 4118 may detect mastitis versus no cell. The same scanning voltage of 500 mV and frequency at 100 kHz were applied. Pure 4118 showed a negative change in capacitance of −1.54% as was indicated in FIG. 20A at −0.9%. On the other hand, 100 dilute 4118 showed a positive change in capacitance of 2.15% and 10 dilute 4118 a positive change in capacitance of 1.27%. FIG. 20C shows a graph of somatic cell count over a five minute test versus change in capacitance over change in time. A strong correlation was observed between the capacitance change rate and somatic cell count in milk, demonstrating that this method is useful for diagnosis of mastitis. In the graph, $y=-1.874 \ln(x)+14.517$ and $R^2=0.8763$. At a good cut-off value of 200K somatic cells/ mL, the sensitivity and specificity of the test are calculated to be 94.7% and 100%, respectively. The result was obtained in five minutes, which is short enough to be used in an in-line system and achieves high accuracy. Similar results were obtained in two other separate experiments. Shorter duration testing is possible by changing test parameters or by giving up some accuracy. In Europe, a somatic cell count of 400 k is used for determining if milk is sellable; in the U.S., the somatic cell count value for determining sellable milk is 750 k. These figures may be utilized in the respective locations for a cut-off for somatic cell count and achieve similar sensitivity and specificity.

Example 4A—Pregnancy Via Anti-PAG Antibody

FIG. 21 illustrates the steps of a process of preparing a SAW electrode array of FIG. 1 for a pregnancy test utilizing a coating of α-PAG (anti-PAG antibody), available from IDEXX, for pregnancy detection. The first step is to treat the SAW array with protein G at 10 μgrams per milliliter in 1×PBS overnight in a humidor at room temperature. Then, the array may be washed once with 0.1×PBST. The α-PAG available from IDEXX is then loaded and kept for approximately one hour at room temperature. Again, the loaded array is washed with 0.1×PBST and then blocked with 0.1×B for approximately 30 minutes to an hour at room temperature.

Testing may comprise loading serum at 1:5 to 1:20 to optimize the dilution as a positive or a negative experimental group. Also, 0.1× buffer B may also be loaded as a control group.

The sweep and data collection process may comprise applying about 5 mV at between forty Hz to 6 MHz for one second to initialize a value of capacitance over frequency. Then, the applied signal may be 100 mV at 100 kHz for an approximately one minute test recording capacitance over time for control and real samples. A processor may then calculate the change in capacitance over time as a function of the initial capacitance sweep.

Figure 22A:
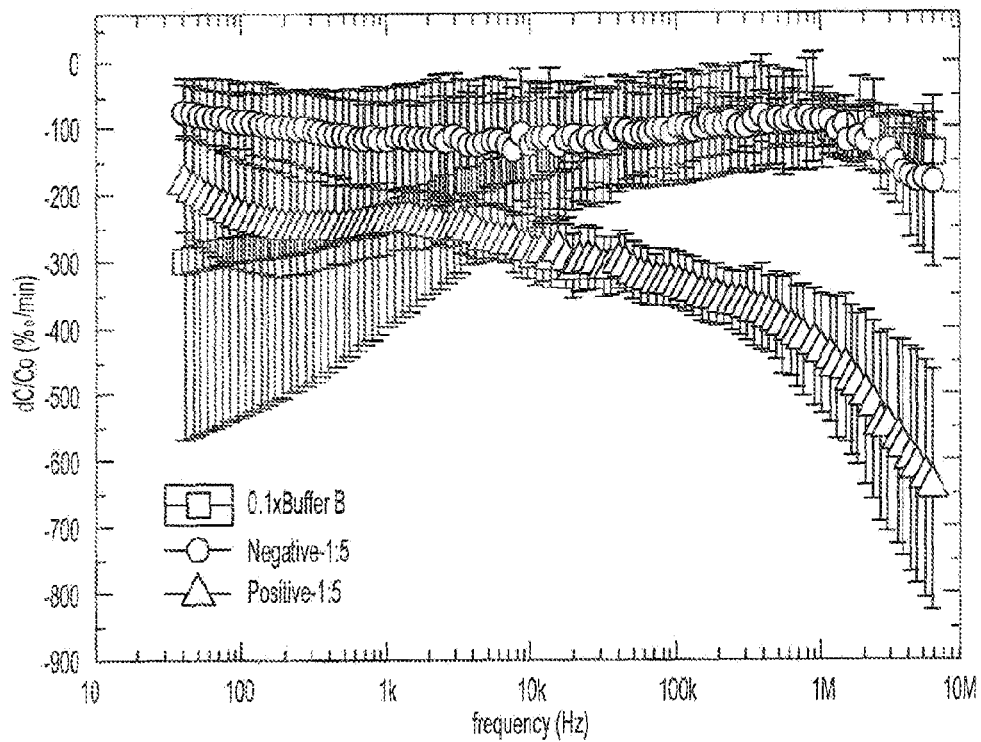
FIGS. 22A and 22B respectively provide graphs of change in capacitance over time versus frequency of applied signal wherein it may be concluded that a signal in the range of 50 kHz and greater may be used to detect pregnancy and a summary of five tests for pregnancy, positive versus negative or buffer solution showing that pregnancy may be detected.
Figure 22B:
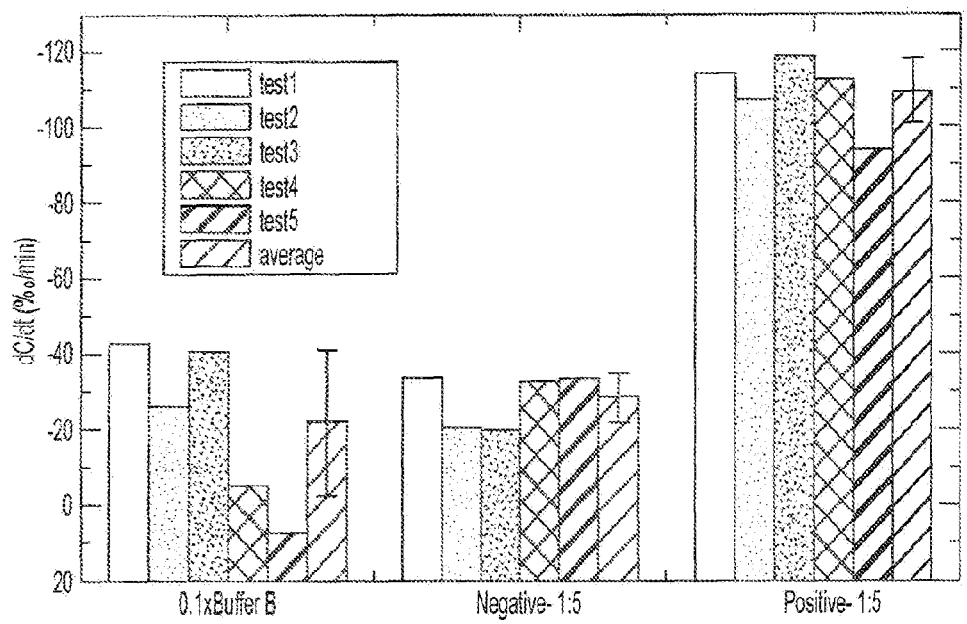

FIGS. 22A and 22B respectively provide respective graphs of change in capacitance over time versus frequency of applied signal wherein it may be concluded that a signal in the range of 50 kHz and greater may be used to detect pregnancy and a summary of five tests for pregnancy, positive versus negative or buffer solution showing that pregnancy may be detected and are shown in summary form.

Limit of Detection Study of Electrode Array Design

Figure 23A:
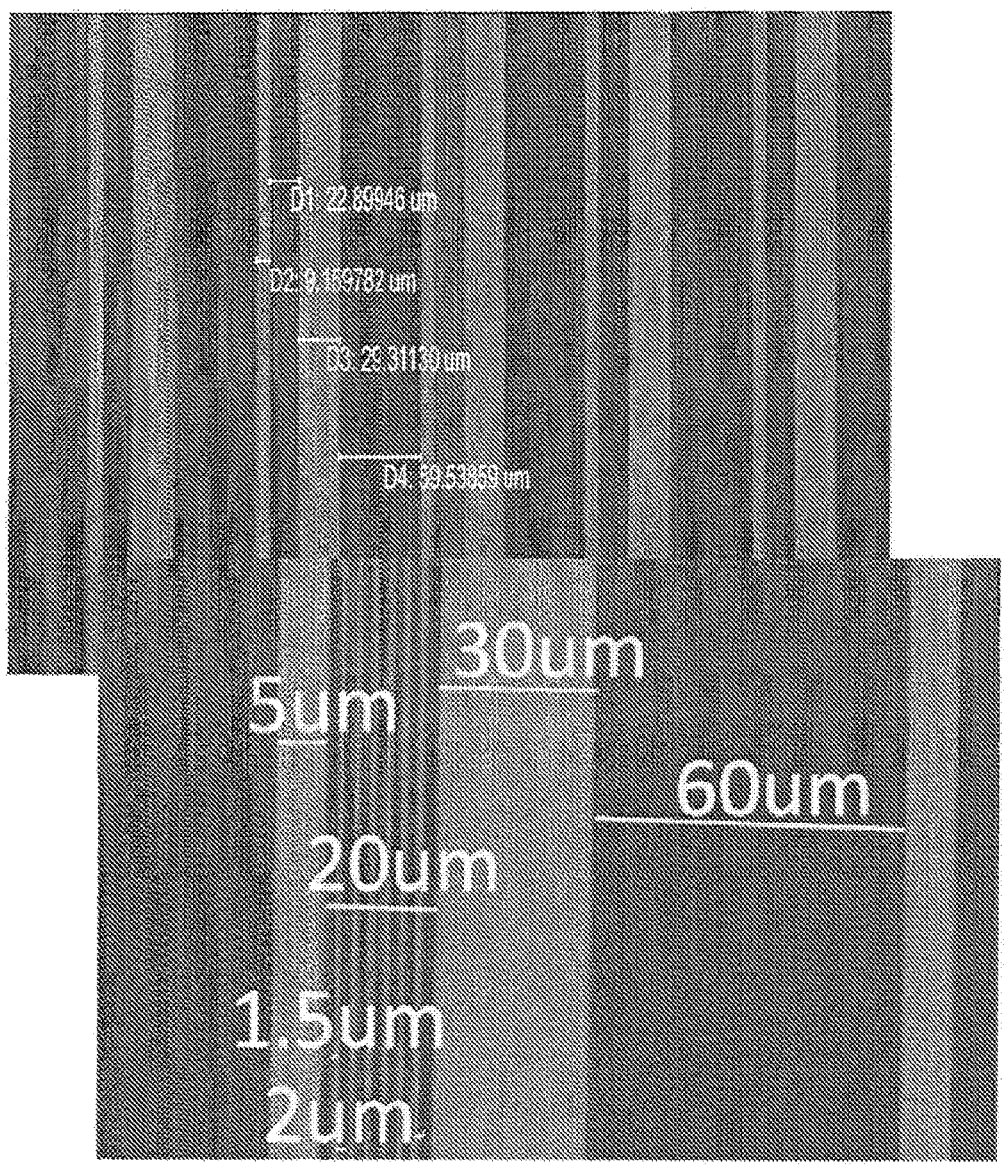
FIG. 23A illustrates an interdigitated electrode array constructed of first providing a plurality of widely spaced electrodes and then for each wide electrode a plurality of very closely spaced electrodes to study the limits of detection of such a constructed electrode array.

FIG. 23A provides a drawing of an interdigitated electrode array constructed of first providing a plurality of widely spaced electrodes and then for each wide electrode a plurality of very closely spaced electrodes to study the limits of detection of such a constructed electrode array. The purpose of the design and testing is to explore the limits of detection of an array structure comprising widely spaced asymmetric electrodes and wide electrodes to attract biomarker to a narrow plurality of parallel symmetric electrodes. The specific dimensions of a wide spacing of asymmetric electrodes reads from top to bottom: D1, the width of a first asymmetric electrode, is 22.89946 μmeters (approximately 20 microns); D2, a first spacing between interdigitated wide asymmetric electrodes is 9.159782 μmeters (approximately 10 microns; D3, a wide spacing between asymmetric interdigitated electrodes of 29.31130 (approximately 30 microns) and D4, the width of the widest asymmetric electrode being 59.53359 μmeters (approximately 60 microns). Then follows a plurality of symmetric narrow width electrodes narrowly spaced and shown in particular detail in a blow-up diagram at the bottom of FIG. 23A. The blow-up shows the flowing spacings and widths of symmetric electrodes: D3 the overall width of the plurality of symmetric electrodes is approximately 30 μmeters; D4 is the spacing between symmetric electrodes of approximately 1.5 μmeters and D2 is the width of one symmetric electrode or approximately 2 μmeters. The limit of detection tests on the new electrodes comprises forming an electrode pattern as a combination of symmetric and asymmetric interdigitated electrodes whereby the asymmetric electrodes may help to generate flow so that more particles are attracted to the symmetric electrodes where they may bind. The asymmetric pattern is roughly 10/20/30/60 and the symmetric pattern is roughly 1.5/1.5/1.5/1.5 (or 2/2/2/2 or an interlaced 1.5/2 pattern).

Figure 23B:
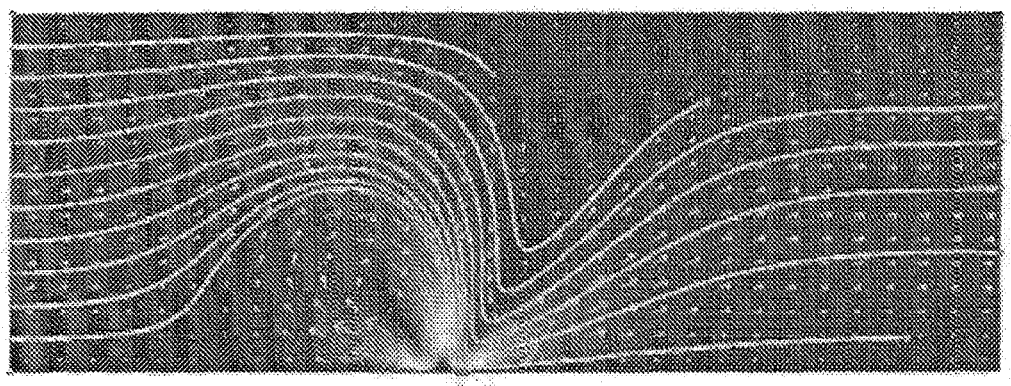
FIG. 23B is a diagram showing the simulated attraction and flows of a particle under the influence of electrokinetic phenomenon to be attracted to the widely spaced electrode and then bind to the very closely spaced electrodes of FIG. 23A.
Figure 23C:
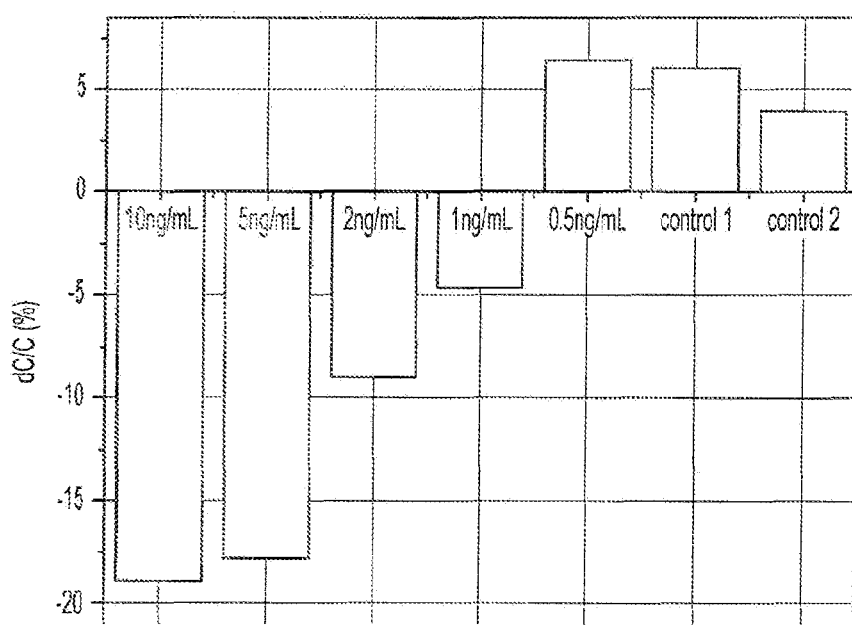
FIG. 23C is a diagram showing improved detection of concentrations of biomarker at, for example, 1 ng per mL, 2 ng per mL and 5 ng/mL, using the interdigitated electrode array of FIG. 23A.

FIG. 23B is a diagram showing the simulated attraction and flows of particles under the influence of electrokinetic phenomenon to be attracted to the widely spaced electrode and then bind to the very closely spaced electrodes. The arrows represent flow and the lines show convection of particles towards the designated area determined by the widely spaced electrodes, where the narrowly spaced electrodes are located. FIG. 23C is a diagram showing improved detection of concentrations of biomarker particles at, for example, 1 ng per mL, 2 ng per mL and 5 ng/mL. The change of capacitance is seen to double from 1 ng/mL concentration to 2 ng/mL concentration and then double again at 5 ng/mL concentration where the test was conducted at an applied signal frequency of 57.5 kHz. Control 1 and 2 are also indicated as exhibiting positive changes in capacitance (as does a small concentration of 0.5 ng/mL). Again, the limit of detection experiment appears to demonstrate that a combination of narrow and wide interdigitated electrodes is preferred to provide an attraction of particles to the symmetric electrodes for binding.

As the above results suggest, the several embodiments of a lab-on-a-chip coated as described and so prepared for receiving a signal of given magnitude, frequency and over a short period of time, such as less than ten minutes, may very likely be used for rapid, in the field or bed-side diagnosis of a number of infectious diseases (via antigen, pathogen, abnormal white cell count) and protein detection, for example, for physical conditions such as pregnancy.

Example 4B—Small Molecule Detection

For small molecule detection, of which progesterone is but one example, the procedure for lab-on-a-chip construction and testing is very similar to that described above. Progesterone level may be a means of testing for pregnancy. The 5/5/25/25 μmeter electrode on a wafer was utilized. However, the impact of treatment with 3-aminopropyl-triethocysilane (APTES) was analyzed to determine if such treatment might have some impact on change rates of capacitance over time.

In particular, for small molecule detection, for example, progesterone, anti-progesterone polyclonal antibody was added in 0.1×PBS on to the electrode surface and allowed to incubate, for example, overnight in a humidor (for example, 4-8, preferably 6 hours is preferable). Once incubated, the electrode may be washed, for example, with PBS-T, for example, three times. Blocking is then performed using 0.1× Buffer B for a period in excess for example, of thirty minutes to be sure the blocking is successful. Then, the blocked electrode with the anti-progesterone polyclonal antibody is washed with PBS-T, for example, three times.

Testing was performed by adding different concentrations of progesterone using plain 0.1× Buffer B as a control starting at 1 ng per milliliter and increasing concentrations of progesterone to as high as 10,000 ng per milliliter in 0.1× Buffer B. In the test at hand, three chips were tested. Concentration level resulted in an increase from the control of no change in capacitance over time to about 4.2 dC/dt (%/min) and then to about 10.1 dC/dt (%/min) for 10 ng per milliliter progesterone. For 10 ng/mL, the CV was 1.7%. Then, when higher concentration levels of progesterone were tested, for example, at 100 ng/milliliter or 1000 ng/milliliter, there was still exhibited a dC/dt %/min of test, but the level reduced to about 2.5 dC/dt suggesting saturation for higher levels of progesterone.

As indicated above, APTES treatment was also attempted and the results were interesting. Specifically, about 2 v/v % APTES in ethanol alcohol was added and allowed to incubate at 63° C. for about 4 hours, then washed with doubly distilled water three times and allowed to dry. An air gun may be used to speed drying. The APTES treated surface dried very quickly with the air gun, and no cluster formed when checked under a microscope.

Then, 2.5% Glutaraldehyde solution was added and allowed to incubate for about two hours at room temperature. The electrode was then washed with double distilled water three times. The electrode was not allowed to dry before adding the progesterone ant-body as described above. Finally, one hundred mM ethanolamine solution was added and allowed to incubate at room temperature for 1 hr. The rest of the preparation for loading with progesterone was the same—blocking with 0.1× Buffer B for longer than thirty minutes and washing with PBS-T.

Progesterone was added to the APTES treated chip in levels between 0 (control) and 1 ng, 0.5 ng, 1 ng, 5 ng, 10 ng and 100 ng per milliliter concentrations in 0.1× Buffer B. Measurements are summarized in the table below where the dC/dt (%/min) was performed at 100 kHz frequency and the voltage level was 500 mV:

TABLE 2

| Concentration | Without APTES | With APTES |
|---|---|---|
| 0 ng/mL control | 1.2019 | 3.886 |
| .5 ng/mL | 2.5754 | 6.3182 |
| 1 ng/mL | 2.989 | 9.7209 |
| 5 ng/mL | 1.3632 | 6.2795 |
| 10 ng/mL | 1.2909 | 5.1568 |

The test results with versus without APTES treatment tend to show that change in capacitance over time go up with APTES versus without and, for example, between 1 ng/mL versus 5 or 10 ng/mL seem to show a less drastic saturation, for example, from 9 to 6 to 5 versus without APTES, the 10 ng/mL result at 1.2909 is little distinguishable from the control at 1.2019. So it may be fairly concluded that APTES treatment as described above may help small molecule detection.

Example 5—D-Dimer as an Indicator of Clotting

Emergency conditions may occur after surgery or during active life. D-dimer is an indicator of clotting. In the following series of tests, a PPy-coated electrode was compared with an un-coated electrode. Preparing the coated chip involved several steps. The chip was cleaned three times with 0.1M diabasic sodium sulfate. Then, the polymer coating solution was prepared by adding 70 μliter of Pyrrole to 930 μliter sodium sulfate to make 0.1M Pyrrole/0.1M sodium sulfate. The polymer was then electrochemically deposited by loading the 0.1 m Pyrrole/0.1M sodium sulfate onto the 5/5/25/25 μmeter wafer. Approximately 1.5 V was applied for about five seconds at room temperature to deposit the coating and the wafer washed twice with PBS. To load or functionalize the Polypryrrole coated chip surface with antigen, anti-D-dimer antibody was loaded as 10 μgram per milliliter in 0.1×PBS and cured for 30 minutes in a humidor at room temperature (humidor optional or if needed). Then, the chip was washed three times with PBST.

The test results occurred by loading D-dimer solutions with a control at no D-dimer at different concentrations in 0.1× Buffer B. 0.1×PBS was used as the test solution. The frequency range tested was between 40 Hz and 6 MHz.

The table below shows the detailed results on Concentration (/mL) for three tests as the test conditions were 500 mv (voltage), 100 kHz (frequency) and 1 minute duration. Units for results are dC/dt (%/min):

TABLE 3

| Concentration(/mL) | Test-1 | Test-2 | Average | std |
|---|---|---|---|---|
| Pbs (control) | 1.5896 | 3.4225 | 2.50605 | .91645 |
| 0 pg | 2.793 | 2.5786 | 2.6858 | .1072 |
| .1 pg | 7.8 | .809 | 4.3045 | 3.4955 |
| 1 pg | 4.904 | 7.8288 | 6.3664 | 1.4624 |
| 10 pg | 25.0948 | 28.5901 | 26.84245 | 1.74765 |
| 100 pg | 36.4224 | 47.1754 | 41.7989 | 5.3765 |
| 1000 pg | 22.2459 | 5.7128 | 13.97935 | 8.26655 |

In D-dimer detection, it appears as if saturation was reached at approximately 100 pg. The test successful test range appears to be between 10 pg and 100 pg with 1000 pg still yielding satisfactory results in comparison with control after saturation is reached.

A control test result is shown below where a sample was dropped directly on PPy coated electrodes without surface functionalization and blocking. The change rates turned out to be very small which tends to rule out the chance of mass non-specific binding:

TABLE 4

| Sample | dC/dt (%/min) |
|---|---|
| 1 pg only | 1.968 |
| 100 pg only | 2.1729 |
| 10000 pg only | 1.216 |

Figure 24A:
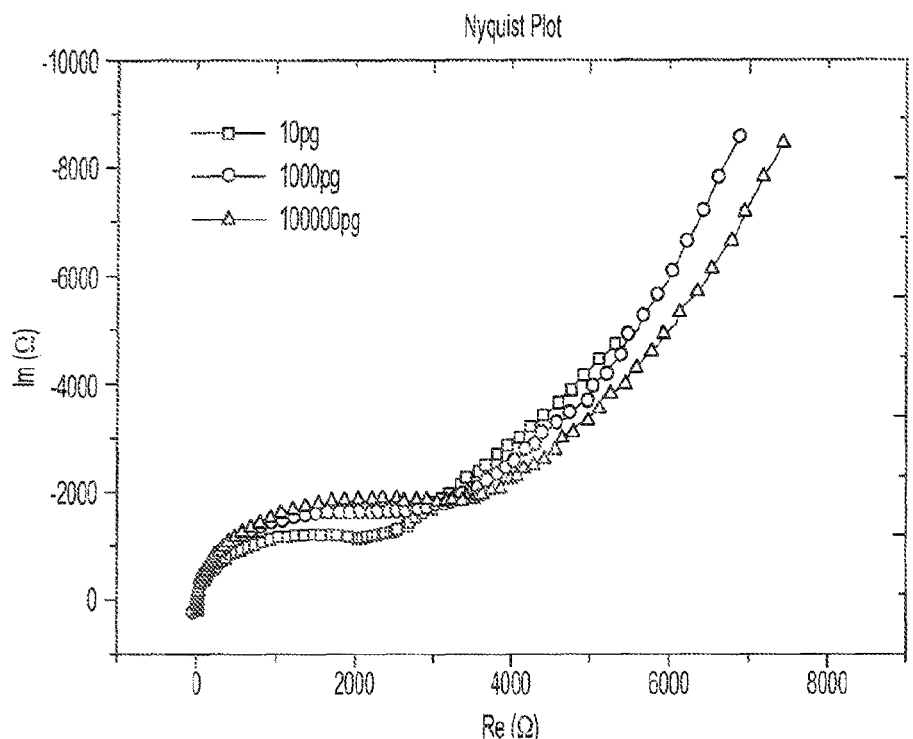
FIGS. 24A and 24B show test results from use of the present invention by Nyquist plots of the imaginary part of the impedance versus the resistance or real-valued part of the impedance with the frequency range tested being 1 kHz to 110 MHz.
Figure 24B:
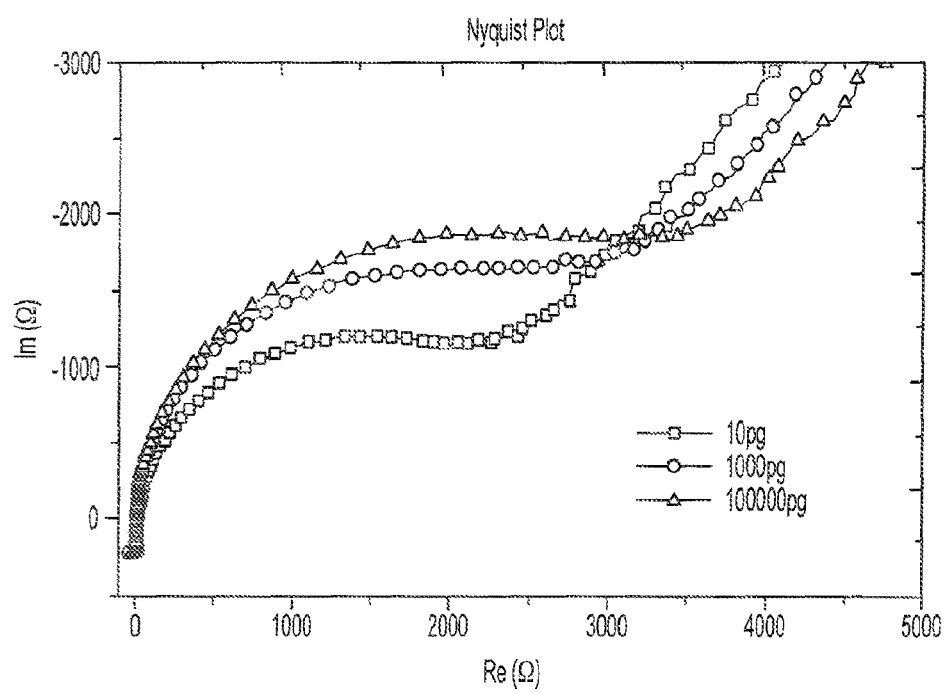

FIGS. 24 A and B show test results by Nyquist plots of impedance versus resistance with the frequency range tested being 1 kHz to 110 MHz. The curves correlate well, for example, for 10 pg concentration per mL. which is demonstrated also by our test results which suggest that, for the moment, 10 to 100 pg may be our detection limit and results above 100 pg exhibit saturation.

Example 6—Sugar (Glucose Detection)

The 5/5/25/25 electrode embodiment was also used for testing for sugar, glucose in particular. A similar process was followed for loading and blocking the chip for sugar testing. For glucose, we used glucose oxidase, an enzyme, as the molecular probe that was loaded on the chip and blocked. The following table is used to show an optimization for testing frequency. As can be seen from the table below, a frequency between 50 and 100 kHz was preferred:

TABLE 5

|         | 1 mg/mL  | .1 mg/mL | 0 mg/mL |
|---------|----------|----------|---------|
| 10 kHz  | −1.7146  | 3.5377   | −2.1191 |
| 50 kHz  | −10.2018 | −7.7705  | −2.9972 |
| 100 kHz | −14.9818 | −10.4084 | −3.3253 |
| 200 kHz | −2.2687  | 0.9512   | −4.4439 |

A table is also shown below wherefrom it may be determined that voltage level was not a significant factor in the testing. Tests were performed for voltage values between 10 mV and 500 mV without the voltage level having much impact on results:

TABLE 6

|          | 10 mv    | 100 mv  | 500 mv  |
|----------|----------|---------|---------|
| 0 mg/mL  | −5.9452  | −8.8171 | −4.9855 |
| .1 mg/mL | −7.7512  | −5.2861 | −6.1618 |
| 1 mg/mL  | 4.9818   | −6.0203 | −6.3895 |
| 10 mg/mL | −11.4325 | −6.4134 | −6.8759 |

The following table provides the test results for glucose detection where the frequency used was 100 kHz, the voltage was 500 mV and an Agilent device was used to apply the voltage at the test frequency chosen:

TABLE 7

|         | Test 1 | Test 2 | Test 3  | average | std    |
|---------|--------|--------|---------|---------|--------|
| 10k μg  | −2.081 | −2.091 | −1.517  | −1.896  | .2679  |
| 1k μg   | −11.09 | −12.01 | −13.38  | −12.16  | .9409  |
| 100 μg  | .8471  | −3.124 | −5.293  | −2.5236 | 2.5425 |
| 10 μg   | −5.868 | −.3218 | −2.795  | −2.9953 | 2.2689 |
| 0 μg    | 6.9314 | 3.1267 | −.6871  | 3.1236  | 3.1102 |

Saturation appears to have been reached at 1000 μg with the results shown as dR/dt (%/min) where R is resistance. As indicated, glucose is but one example of a sugar that may be similarly tested. One suggested application of sugar detection, e.g., sucrose, is in the detection of sugar in beer in addition to medical applications (e.g., glucose).

Example 7—Enzymatic Redox Reaction Detection

Enzymatic redox reactions have been used for diagnosis of diseases or detection of molecules in solution. An enzymatic redox reaction generally involves a reaction between an enzyme and a substrate, producing ions that change the conductivity of the solution. The change in conductivity may be detected electrochemically, for example, by measuring a change in a current flowing through the solution.

There are at least three different ways that enzymatic redox reactions may be used for diagnosis of diseases through electrochemical detection—detection of a substrate, detection of an enzyme, and detection of a probe.

An example of substrate detection is using the diagnostic redox enzyme glucose oxidase, which catalyzes conversion of glucose (substrate) to gluconolactone while producing hydrogen peroxide. The level of hydrogen peroxide can be electrochemically measured as a surrogate of glucose level in the sample. This reaction is the basis for measurement of glucose (substrate) level which elevates in patients with diabetes. Normal level of glucose in blood is 5 mM and detection limit of glucose based on this principle is reported to range from 1 nM to 25 μM.

An example of enzyme detection is when lactate dehydrogenase (LDH), which is a marker of general tissue damage, catalyzes conversion of aspartate to glutamate. When glutamate is converted to ketoglutarate by glutamate oxidase, hydrogen peroxide is produced as a side product and can be detected electrochemically as mentioned above. Normal level of LDH is 3 nM and detection limit of a commercial test is 30 pM.

As for probe detection, when a probe of a target analyte (such as aptamer) is conjugated with a redox enzyme inhibitor, such a conjugate inhibits reaction of redox enzyme only in the absence of the analyte, and, therefore, can be used to measure the level of the analyte in a solution. This can be used not only for disease diagnosis, but also for other purposes such as chemical contaminants in environmental samples.

These three concepts may be applied to the lab-on-a-chip for sensitive and rapid diagnosis. The lab-on-a-chip may detect a change in interfacial capacitance due a change of conductivity of the sample solution resulting from enzymatic redox reactions close to the surface of the electrodes. The electrode array may be functionalized/coated with either linker molecules specific to diagnostic redox enzymes (for enzyme detection) or redox enzymes themselves (for substrate or probe detection). A low AC voltage signal may be applied to the electrode array to induce ACEK effects that create convection of target molecules (e.g., enzymes, substrates, and/or probes) towards the surface of the electrode array, promoting redox reaction catalyzed by enzymes captured by the linker molecules (enzyme detection) or the immobilized enzymes (substrate or probe detection). The redox reaction specific to the enzyme-substrate pair may be detected by measuring the change in interfacial capacitance at the surface of the electrode array.

Figure 25A:
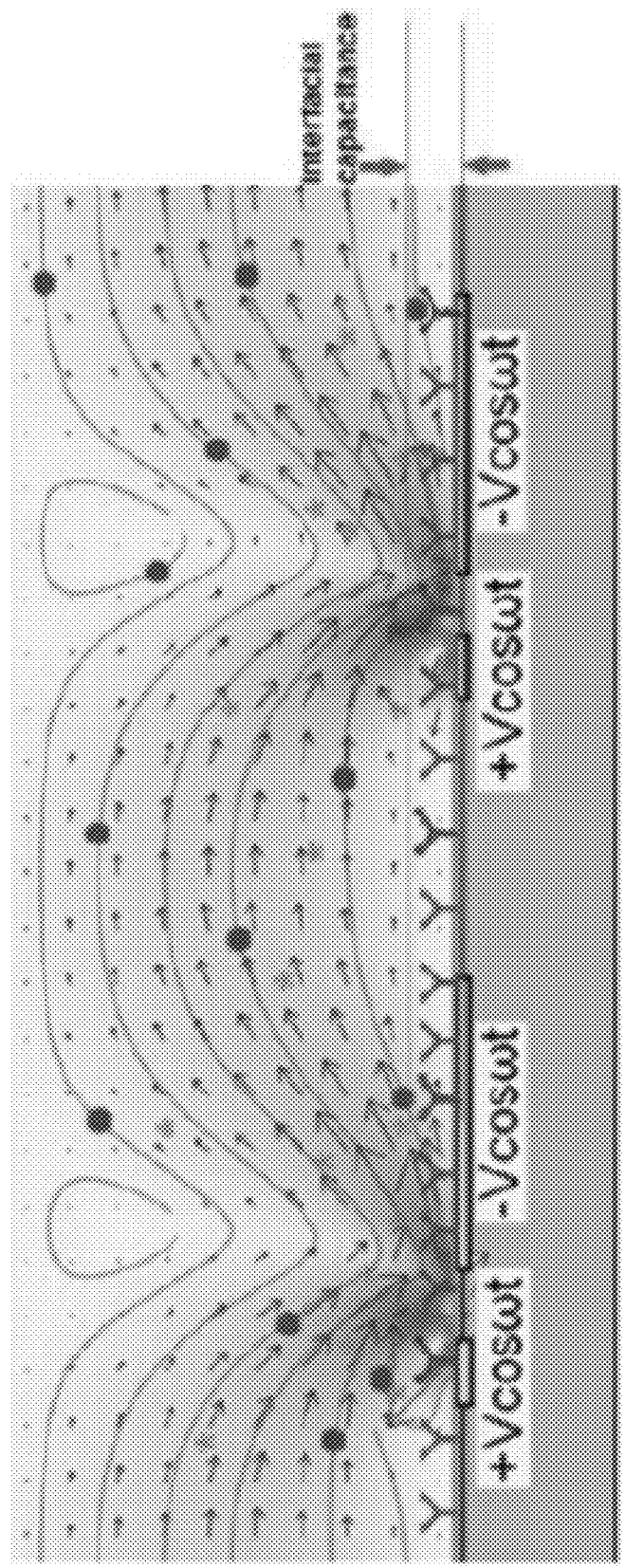
FIG. 25A is a conceptual drawing illustrating the detection of redox enzyme by AC capacitive sensing.

FIG. 25A is a conceptual drawing illustrating the detection of redox enzyme by AC capacitive sensing. An antibody, appearing as Y-shaped receptors (i.e., linker molecules) and immobilized on the electrodes, captures a specific enzyme (shown as ●), which then catalyzes redox reaction with a substrate (shown as *) in the sample solution/electrolyte. The reaction happens at the electrolyte/electrode interface and can be detected by a change in the interfacial capacitance.

Figure 25B:
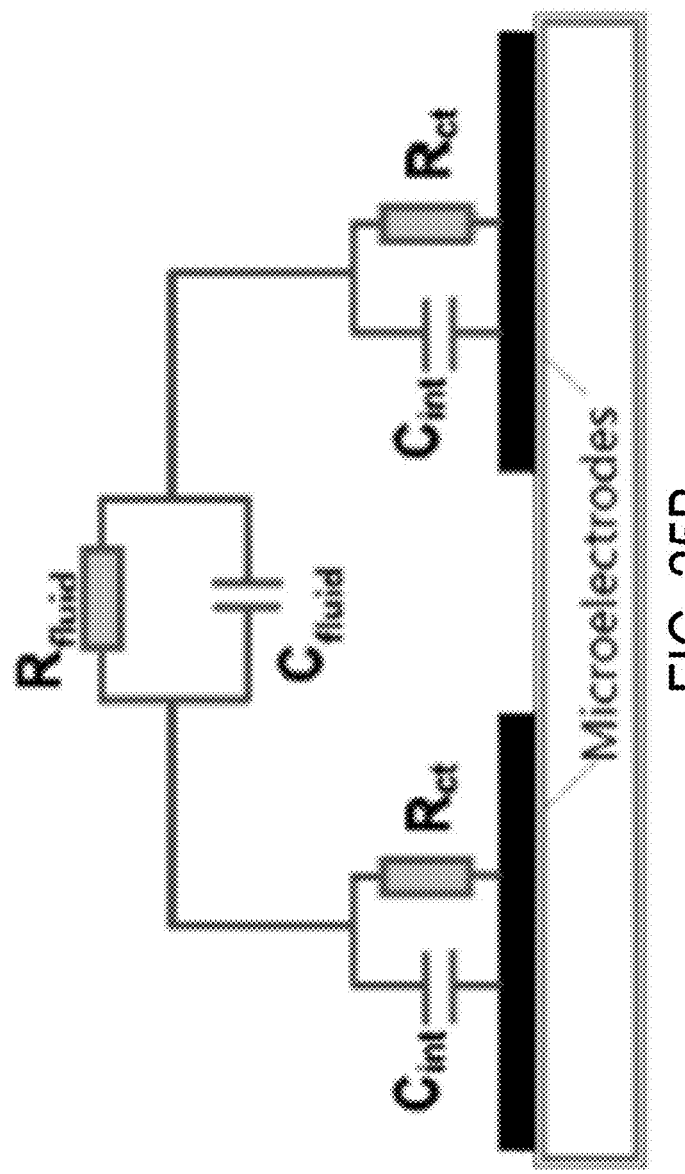
FIG. 25B is a representative equivalent circuit of the 'electrolyte-electrode' system of FIG. 25A.

FIG. 25 B is a representative equivalent circuit of the 'electrolyte-electrode' system of FIG. 25A. A charge transfer resistance $R_{ct}$ and an interfacial capacitance $C_{int}$ may account for charge transport at the electrode/electrolyte interface. In FIG. 25B, the electrolyte resistance is represented as $R_{fluid}$ and the electrolyte capacitance as $C_{fluid}$. Enzymatic reaction causes charge transfer across the biopolymer layer on the electrode. Electrically, this phenomenon may be illustrated as $R_{ct}$ going down and $C_{int}$ going up. By monitoring $C_{int}$, the lab-on-a-chip focuses on the process taking place close to electrode surface. As the enzymatic reaction continues, $C_{int}$ increases continuously. Higher sensitivity is expected for this method due to enzymatic amplification and interfacial capacitance measurement.

The interfacial capacitance $C_{int}$ is the indicator of the enzymatic redox reaction. $C_{int}$ is indicative only of changes at sensor surface, as illustrated by the equivalent circuit of FIG. 25B. As such, the detection is highly localized around the interface where enzyme reactions take place. The response is not an average of ionic environment between the electrodes as with conventional electrochemical detection. Consequently, using the lab-on-a-chip to detect enzymatic redox reactions is more sensitive. Additionally, the effect of interferences in a complex fluid mostly shows up through the fluid resistance $R_{fluid}$. Such interferences can be easily eliminated when only $C_{int}$ is measured. Consequently, high sensitivity and specificity are expected when using the lab-on-a-chip to detect enzymatic redox reactions.

The detection is done at a fixed frequency, which allows for simultaneous induction of ACEK convection of molecules (including substrates and products) and interfacial capacitance measurement. At frequencies commonly used for ACEK, the impedance may be approximated as a serial connection of $C_{int}$ and $R_{fluid}$, allowing for direct extraction of $C_{int}$ without resorting to complicated data processing or instrumentation.

Moreover, with a detection metric that uses a change rate of normalized $C_{int}$, baseline drift or the need for a reference sensor/reference sample may be avoided, greatly simplifying the detection procedure and instrumentation. Requirements on instrument precision may also be relaxed, minimizing the effect of differences between sensors and allowing the system to be built at affordable prices.

Figure 25C:
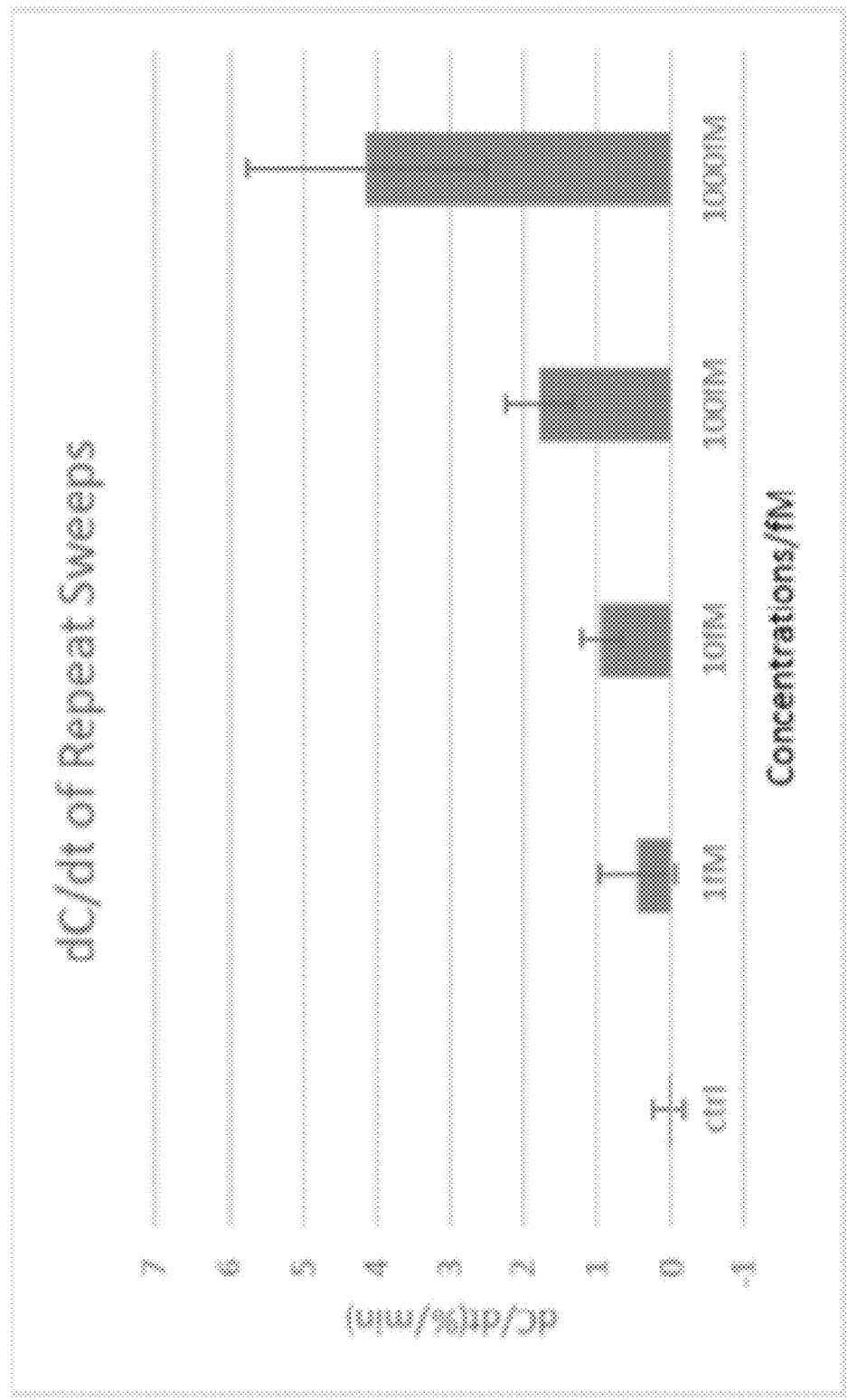
FIG. 25C shows experimental results for substrate detection using electrodes functionalized with an enzyme, for different concentrations of the substrate.

FIG. 25C shows experimental results for substrate detection using electrodes functionalized with an enzyme, for different concentrations of the substrate. The substrate in the solutions is Tetramethilbenzidine Dihydrochloride Dihydrate (TMB) (M.W.=349.3, MP Biomedicals, LLC, Cat. No.: 152116). The enzyme immobilized on the electrodes is Horseradish Peroxidase (HRP) (Thermo Scientific, No.: 31490). The electrode surface was blocked with 0.01% Triton for half an hour. The experiment was carried out with a 20-kHz, 100-mV AC signal. FIG. 25C shows the normalized dC/dt recorded for 1 fM, 10 fM, 100 fM and 1000 fM (1 pM) of TMB samples. As can be seen, the normalized dC/dt increases proportionally with the increase in substrate concentration.

Detection Amplification with Labeling Particles

The limit of detection (LOD) of the lab-on-a-chip has been found to be dependent on the size of the target molecules or analytes. Specifically, LOD decreases as the size of the analytes increases. For example, when testing specific proteins, which are about 10 nm in size, the LOD was about 1 ng/mL, while the LOD was about 1 pg/mL when detecting virus particles that are about 100 nm in size.

As such, the detection of small sample analytes may be amplified (i.e., the LOD may be decreased) by conjugating the small sample analytes with nano- to micro-size particle labels and then loading the conjugated sample onto the electrodes of the lab-on-a-chip. The labeling particles are functionalized with linker molecules specific to target analytes prior to the assay. A known concentration of labeling particles is mixed with the sample solution. The mixture is incubated for the labeling particles to conjugate with the target analytes. The conjugated sample is loaded onto the electrode for testing. The labeling particles may be latex beads, magnetic beads, or microorganisms such as virus, bacteria. FIGS. 26A, 26B, and 26C are depictions of sample analytes, a labeling particle, and a conjugated sample, respectively.

Figure 26D:
FIGS. 26D, 26E, and 26F are conceptual schematics illustrating a coated/functionalized electrode surface, analyte detection at a coated electrode surface, and conjugated sample detection at a coated electrode surface, respectively.
Figure 26E:
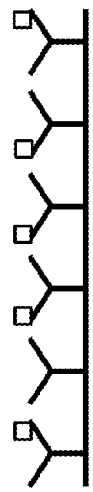
Figure 26F:
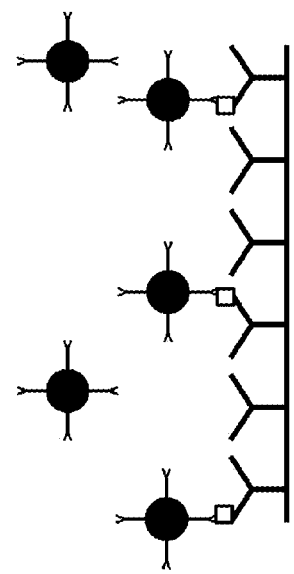
Figure 26A:
FIGS. 26A, 26B, and 26C depict sample analytes, a labeling particle, and a conjugated sample, respectively.
Figure 26B:
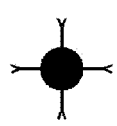
Figure 26C:
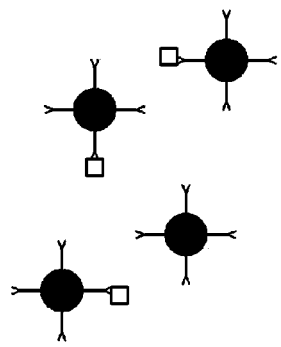

FIG. 26D depicts a coated/functionalized electrode of a lab-on-a-chip. FIG. 26E illustrates analytes, without labeling particles, binding to the coated electrode. Here, the change in impedance or capacitance of the electrode is due to the addition of the analytes. Such a change in capacitance may be small for diluted concentration of analytes. On the other hand, FIG. 26F illustrates conjugated samples binding to the coated electrode. In this case, both the analytes and the labeling particles contribute to the change in impedance or capacitance, thus amplifying the detection of the lab-on-a-chip.

The present lab-on-a-chip may also be used to detect enzyme levels in a manner faster than ELISA or other laboratory methods. Above, the enzyme, glucose oxidase was discussed for diagnosis of diabetes. Certain tissue cells (such as organ tissue cells) contain characteristic enzymes which enter the blood only when the cells to which they are confined are damaged or destroyed. One example of an enzyme that may be tested for in animal blood is aldolase which may be symptomatic of skeletal muscle damage at high serum levels in the blood and progressive muscular dystrophy. Also, aldolase levels may be slightly increased in early stages of viral hepatitis and advance prostate cancer (males). Creatine Phosphokinase (CPK) is another enzyme which may be measured by lab-on-a-chip from blood samples and may be a valuable for differentiating diagnostic information related to heart attacks or indicative of skeletal muscle damage. GGT is an enzyme symptomatic of obstructive diseases of the biliary tract and liver cancers. Lactic Dehydrogenase (LDH) can be further separated into five components or isoenzymes LDH-1, LDH-2, LDH-3, LDH-4 and LDH-5. Differential levels of these isoenzymes may be indicative of liver or muscle disease. An LDH-1 level higher than that of LDH-2 may be indicative of a recent heart attack or heart injury. Since total LDH level rises within 24 to 48 hours after a heart attack, LDH level testing is a useful tool for delayed diagnosis of a heart attack. Other enzyme levels that may be tested for via lab-on-a-chip include Lipase for pacreatatitis, GOT for heart angina or liver damage (including cirrhosis) and biliary obstruction.

Testing of well water typically involves the testing for bacteria content, in particular, coliform and *E. coli*. The present lab-on-a-chip invention may find commercial application for well water testing for bacteria.

A list of infectious diseases that may be similarly diagnosed comprise HIV, Hepatitis B and C, SARS, *Helicobacter pylori* infections, Leprosy, Lyme disease, Toxoplasmosis, Newcastle disease, Foot-and-mouth disease, Porcine parvovirus, Pseudorabies, Avian influenza, Porcine Reproductive and Respiratory Syndrome, brucellosis and, also, Crohn's disease. Considerable evidence exists that MAP is also a causative organism of Crohn's disease in humans, and some MAP antigens, p35 and p36 in particular, were found to be reactive in a majority (95%) of Crohn's disease patients' blood samples as reported by Ira Shafran et al., September, 2002, *Digestive Diseases and Sciences*, pp. 2079-2081. Also, antibodies against *Saccharomyces cerevisiae* (ASCA/neutrophilic cytoplasm (ANCA) are known to be indicators of Crohn's disease and used in commercial immunoassay kits available from Orgentec and The Doctors Doctor. The ASCA/ANCA immunoassays are used for differential diagnosis of ulcerative colitis and Crohn's disease with similar symptoms. Consequently, the present lab-on-a-chip embodiments may have application in the diagnosis of Crohn's disease in humans.

While various aspects of the present invention have been described above, it should be understood that they have been presented by way of example and not limitation. It will be apparent to persons skilled in the relevant art(s) that various changes in form and detail can be made therein without departing from the spirit and scope of the present invention. Thus, the present invention should not be limited by any of the above described exemplary aspects, but should be defined only in accordance with the following claims and their equivalents.

In addition, it should be understood that the figures in the attachments, which highlight the structure, methodology, functionality and advantages of the present invention, are presented for example purposes only. The present invention is sufficiently flexible and configurable, such that it may be implemented in ways other than that shown in the accompanying figures. Any patent applications, patents or articles references herein are deemed incorporated by reference as to any material deemed necessary for an understanding of the embodiments and methods described herein.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present invention in any way.

What is claimed is:

1. A method for detecting a biomarker in a sample, comprising:
    functionalizing an electrode array by coating the electrode array with a coating material, the electrode array comprising a plurality of electrodes;
    applying the sample onto the electrode array;
    controlling, using a controller, an impedance read-out circuit to measure an initial value of an impedance of the electrode array when the sample is initially applied;
    controlling, using a controller, a signal generator coupled to the electrode array to generate an electrical signal and apply the electrical signal to the electrode array after the initial value of the impedance is measured, the electrical signal having a fixed magnitude and a fixed frequency;
    controlling, using the controller, the impedance read-out circuit to measure the impedance versus time of the electrode array for a predetermined period of time after the initial value of the impedance is measured; and
    calculating a change in the impedance versus time of the electrode array with respect to the initial value of the impedance.

2. The method of claim 1, further comprising, when the change in the impedance of the electrode array exceeds a predetermined threshold, indicating the presence of a disease or a condition.

3. The method of claim 1, further comprising, when the change in the impedance of the electrode array exceeds a predetermined threshold, indicating the presence of one of the following: Johne's disease, mastitis, pregnancy, tuberculosis, clotting, heart attack, influenza and diabetes.

4. The method of claim 1, wherein the coating material comprises a molecule that binds to the biomarker.

5. The method of claim 1, wherein the coating material comprises a molecule that reacts with the biomarker.

6. The method of claim 1, wherein the coating material comprises one or more of an antigen, an antibody, a protein, a peptide, a nucleic acid, a lipid, and an enzyme.

7. The method of claim 1, wherein the biomarker is one or more of an antigen, an antibody, a protein, a peptide, a nucleic acid, a hormone, a lipid, a sugar, and a probe molecule.

8. The method of claim 1, further comprising, prior to applying the sample onto the electrode array:
    mixing the sample with a predetermined concentration of labeling particles, the labeling particles being functionalized with linker molecules specific to the biomarker; and
    incubating the mixture of the sample and the labeling particles.

9. The method of claim 8, wherein the labeling particles is one of latex beads, magnetic beads, and microorganisms.

10. The method of claim 1, further comprising, prior to functionalizing the electrode array, coating the electrode array with a pre-coating material.

11. The method of claim 10, wherein the pre-coating material is 3-aminopropyl-triethoxysilane or polypyrrole.

12. The method of claim 1, wherein the electrical signal is a voltage signal having a magnitude less than 10 Vrms and a frequency less than 10 MHz.

13. The method of claim 1, wherein the electrode array is provided in an integrated circuit.

14. The method of claim 1, wherein the predetermined period of time is less than 10 minutes.

15. The method of claim 1, wherein the sample is applied to the electrode array only once.

16. The method of claim 1, wherein the electrode array is a coplanar electrode array.

17. The method of claim 1, wherein the plurality of electrodes in the electrode array are parallel plate electrodes.

* * * * *